United States Patent
Sinnott et al.

(10) Patent No.: US 12,226,129 B2
(45) Date of Patent: Feb. 18, 2025

(54) FASTENING DEVICES, SYSTEMS, AND METHODS

(71) Applicant: RTG Scientific, LLC, Austin, TX (US)

(72) Inventors: Mary Sinnott, Logan, UT (US); Andrew Fauth, North Logan, UT (US)

(73) Assignee: RTG SCIENTIFIC, LLC, Austin, TX (US)

( * ) Notice: Subject to any disclaimer, the term of this patent is extended or adjusted under 35 U.S.C. 154(b) by 172 days.

(21) Appl. No.: 17/668,320

(22) Filed: Feb. 9, 2022

(65) Prior Publication Data

US 2022/0323131 A1  Oct. 13, 2022

Related U.S. Application Data

(60) Provisional application No. 63/147,640, filed on Feb. 9, 2021.

(51) Int. Cl.
*A61B 17/86* (2006.01)
*A61B 17/68* (2006.01)
(Continued)

(52) U.S. Cl.
CPC ........ *A61B 17/704* (2013.01); *A61B 17/7032* (2013.01); *A61B 17/7034* (2013.01);
(Continued)

(58) Field of Classification Search
CPC .... A61B 17/863; A61B 17/7225; F16B 33/02
See application file for complete search history.

(56) References Cited

U.S. PATENT DOCUMENTS

| 186,904 | A | * | 1/1877 | Vanstone et al. | ...... B21D 53/44 411/394 |
| 1,075,310 | A | * | 10/1913 | Ulrich | ..................... F16B 39/30 411/938 |

(Continued)

FOREIGN PATENT DOCUMENTS

| GB | 2033755 A | 5/1980 |
| WO | 2004098442 A1 | 11/2004 |

(Continued)

OTHER PUBLICATIONS

International Search Report dated Aug. 10, 2023 for corresponding PCT/US2023/020900.

(Continued)

*Primary Examiner* — David W Bates
(74) *Attorney, Agent, or Firm* — David Meibos; Maywood IP Law

(57) ABSTRACT

A compression fastener may include a shaft and a helical thread disposed about the shaft. The shaft may include a proximal end, a distal end, a proximal shaft portion, and a distal shaft portion. The helical thread may include at least one concave undercut surface and a plurality of pitches that may include at least one first pitch along the proximal shaft portion and at least one second pitch along the distal shaft portion. The at least one concave undercut surface may be angled towards one of the proximal end and the distal end of the shaft, and the at least one first pitch and the at least one second pitch may not be equal to each other.

24 Claims, 12 Drawing Sheets

(51) Int. Cl.
*A61B 17/70* (2006.01)
*A61B 17/72* (2006.01)
*A61F 2/40* (2006.01)
A61B 17/00 (2006.01)
A61B 17/56 (2006.01)
A61F 2/30 (2006.01)

(52) U.S. Cl.
CPC ........ *A61B 17/7037* (2013.01); *A61B 17/725* (2013.01); *A61B 17/8605* (2013.01); *A61B 17/8625* (2013.01); *A61B 17/863* (2013.01); *A61F 2/4014* (2013.01); *A61F 2/4081* (2013.01); *A61B 2017/00477* (2013.01); *A61B 2017/00526* (2013.01); *A61B 2017/564* (2013.01); *A61B 2017/681* (2013.01); *A61F 2002/30332* (2013.01); *A61F 2220/0033* (2013.01)

(56) References Cited

U.S. PATENT DOCUMENTS

| | | | |
|---|---|---|---|
| 1,876,796 A * | 9/1932 | Trbojevich | F16B 33/02 411/423 |
| 2,788,046 A * | 4/1957 | Rosan | F16B 39/30 411/311 |
| 3,046,828 A * | 7/1962 | Dzus | F16B 5/0208 411/965 |
| 3,848,276 A | 11/1974 | Martinez | |
| 4,175,555 A * | 11/1979 | Herbert | A61B 17/863 606/304 |
| 4,334,814 A * | 6/1982 | McKewan | B21H 3/027 411/311 |
| 4,810,149 A * | 3/1989 | Lee | F16B 33/02 411/366.3 |
| 4,966,345 A * | 10/1990 | Bersier | E04G 25/06 248/354.3 |
| 5,964,768 A | 10/1999 | Huebner | |
| 6,030,162 A * | 2/2000 | Huebner | A61B 17/8863 411/413 |
| 6,315,564 B1 * | 11/2001 | Levisman | A61B 17/8625 606/315 |
| 6,319,254 B1 * | 11/2001 | Giet | A61B 17/8875 606/104 |
| 6,800,078 B2 | 10/2004 | Reed | |
| 7,281,925 B2 * | 10/2007 | Hall | A61C 8/0022 606/314 |
| 7,537,603 B2 | 5/2009 | Huebner et al. | |
| 8,075,604 B2 * | 12/2011 | Denis | A61B 17/7041 606/315 |
| 8,128,671 B2 * | 3/2012 | Taylor | A61B 17/863 606/315 |
| 8,147,531 B2 * | 4/2012 | Corrao | A61B 17/863 606/301 |
| 8,337,205 B2 * | 12/2012 | Reed | A61C 8/0086 433/174 |
| 8,602,781 B2 * | 12/2013 | Reed | A61C 8/0022 606/301 |
| 8,870,928 B2 * | 10/2014 | Jackson | A61B 17/7032 606/273 |
| 8,875,399 B2 | 11/2014 | Reed | |
| 8,911,478 B2 * | 12/2014 | Jackson | A61B 17/683 606/246 |
| 9,079,263 B2 * | 7/2015 | Reed | A61B 17/8635 |
| 9,526,547 B2 | 12/2016 | Reed | |
| 9,687,319 B2 * | 6/2017 | Reed | A61C 8/0018 |
| 9,782,209 B2 | 10/2017 | Reed | |
| 9,901,379 B2 | 2/2018 | Reed | |
| 10,064,707 B2 * | 9/2018 | Zadeh | A61B 17/863 |
| 10,085,782 B2 * | 10/2018 | Reed | A61B 17/864 |
| 10,265,177 B2 | 4/2019 | Quinn et al. | |
| 10,441,385 B2 | 10/2019 | Reed | |
| 10,639,086 B2 | 5/2020 | Reed | |
| 10,687,877 B2 | 6/2020 | Lavigne et al. | |
| 11,278,335 B2 * | 3/2022 | Rowe | A61B 17/8635 |
| 11,382,724 B2 * | 7/2022 | Barton | A61C 8/0022 |
| 2003/0088248 A1 | 5/2003 | Reed | |
| 2004/0162560 A1 * | 8/2004 | Raynor | F16B 33/02 403/362 |
| 2004/0167523 A1 * | 8/2004 | Jackson | A61B 17/7091 606/273 |
| 2004/0210227 A1 * | 10/2004 | Trail | A61B 17/8635 606/328 |
| 2006/0204930 A1 | 9/2006 | Sul | |
| 2006/0222475 A1 * | 10/2006 | Breihan | E21B 17/042 411/411 |
| 2007/0233123 A1 * | 10/2007 | Ahmad | A61B 17/864 606/307 |
| 2008/0219800 A1 * | 9/2008 | Van Cor | F16B 33/02 411/386 |
| 2009/0069852 A1 | 3/2009 | Farris et al. | |
| 2009/0305189 A1 | 12/2009 | Scortecci et al. | |
| 2010/0094358 A1 | 4/2010 | Moore et al. | |
| 2010/0121327 A1 | 5/2010 | Velikov | |
| 2010/0172717 A1 * | 7/2010 | Corbett | F16B 33/00 411/366.1 |
| 2011/0288650 A1 | 11/2011 | Ries et al. | |
| 2012/0022603 A1 * | 1/2012 | Kirschman | A61B 17/863 606/305 |
| 2012/0130433 A1 * | 5/2012 | Huebner | A61B 17/8863 606/300 |
| 2013/0053901 A1 * | 2/2013 | Cormier | A61B 17/7032 606/305 |
| 2013/0136533 A1 * | 5/2013 | Choi | F16B 7/18 72/199 |
| 2013/0253517 A1 | 9/2013 | Mitchell et al. | |
| 2014/0023990 A1 | 1/2014 | Zadeh | |
| 2014/0056460 A1 | 2/2014 | Barnes | |
| 2014/0058460 A1 * | 2/2014 | Reed | A61B 17/863 606/301 |
| 2014/0326448 A1 * | 11/2014 | Pacheco | F16B 33/02 166/242.6 |
| 2014/0329202 A1 * | 11/2014 | Zadeh | A61C 8/006 433/174 |
| 2015/0201984 A1 * | 7/2015 | Orbay | A61B 17/8625 606/304 |
| 2015/0313658 A1 * | 11/2015 | Kolb | A61B 17/8625 606/309 |
| 2018/0303529 A1 * | 10/2018 | Zastrozna | A61B 17/8635 |
| 2018/0335070 A1 | 11/2018 | May | |
| 2019/0038426 A1 | 2/2019 | Ek | |
| 2019/0105131 A1 * | 4/2019 | Barton | A61C 8/0025 |
| 2019/0223917 A1 * | 7/2019 | Gray | A61B 17/7082 |
| 2019/0358039 A1 | 11/2019 | Ducharme et al. | |
| 2021/0259842 A1 * | 8/2021 | Feng | A61B 17/7001 |
| 2022/0151670 A1 * | 5/2022 | Hyer | B23G 5/18 |
| 2022/0152715 A1 * | 5/2022 | Hyer | B23G 5/18 |
| 2022/0249147 A1 * | 8/2022 | White | A61B 17/8625 |
| 2022/0249148 A1 | 8/2022 | Hyer et al. | |

FOREIGN PATENT DOCUMENTS

| | | |
|---|---|---|
| WO | 2007074498 A2 | 7/2007 |
| WO | 2019238085 A2 | 12/2019 |
| WO | 2020224657 A2 | 11/2020 |

OTHER PUBLICATIONS

International Search Report dated Jul. 5, 2023 for corresponding PCT/US2023/018561.
U.S. Appl. No. 10/085,782, filed Oct. 2, 2018, Reed.
International Search Report and Written Opinion dated Jul. 6, 2022 for corresponding PCT Application No. PCT/US2022/015866.

* cited by examiner

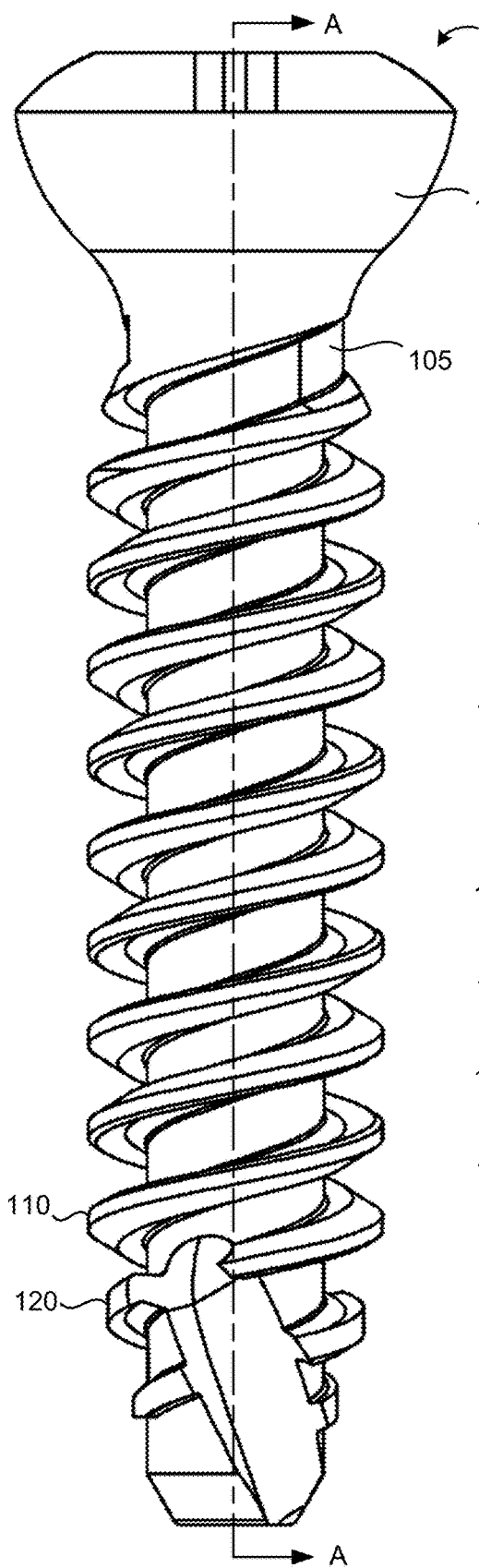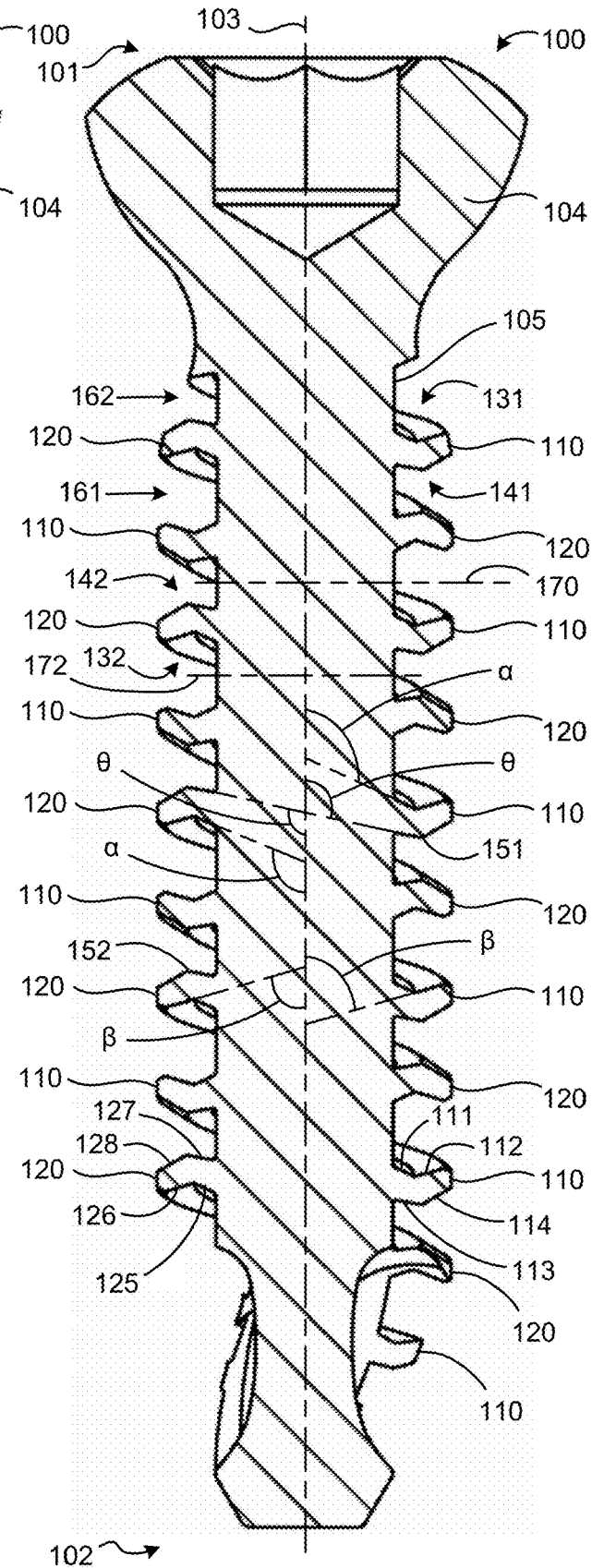
FIG. 1C
FIG. 1D

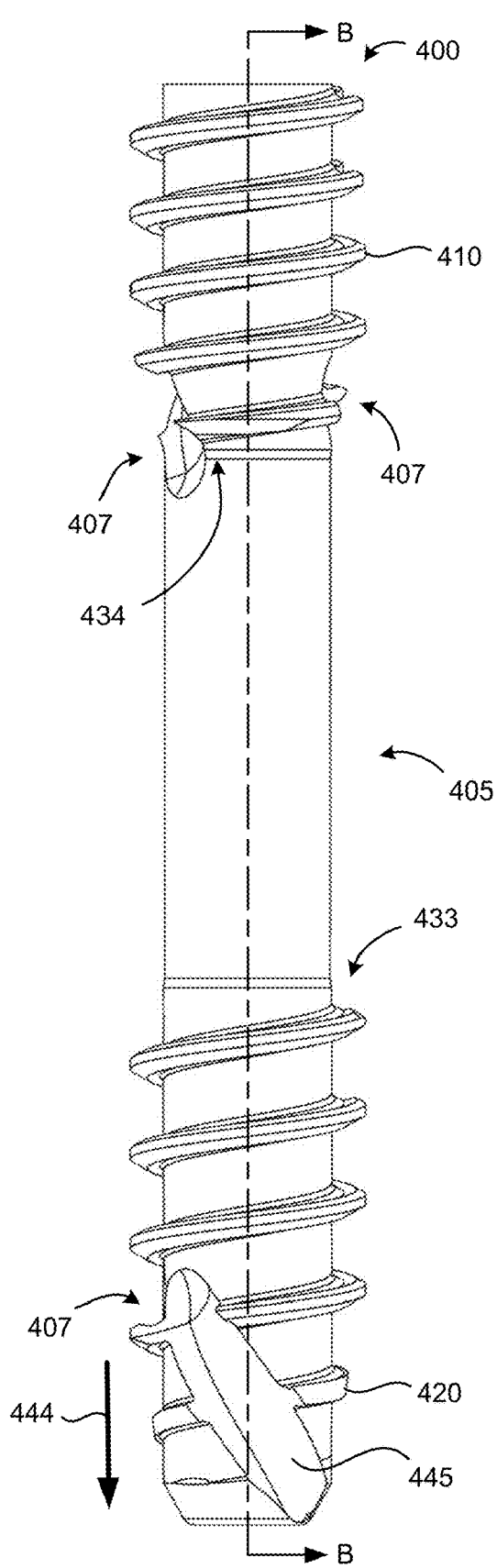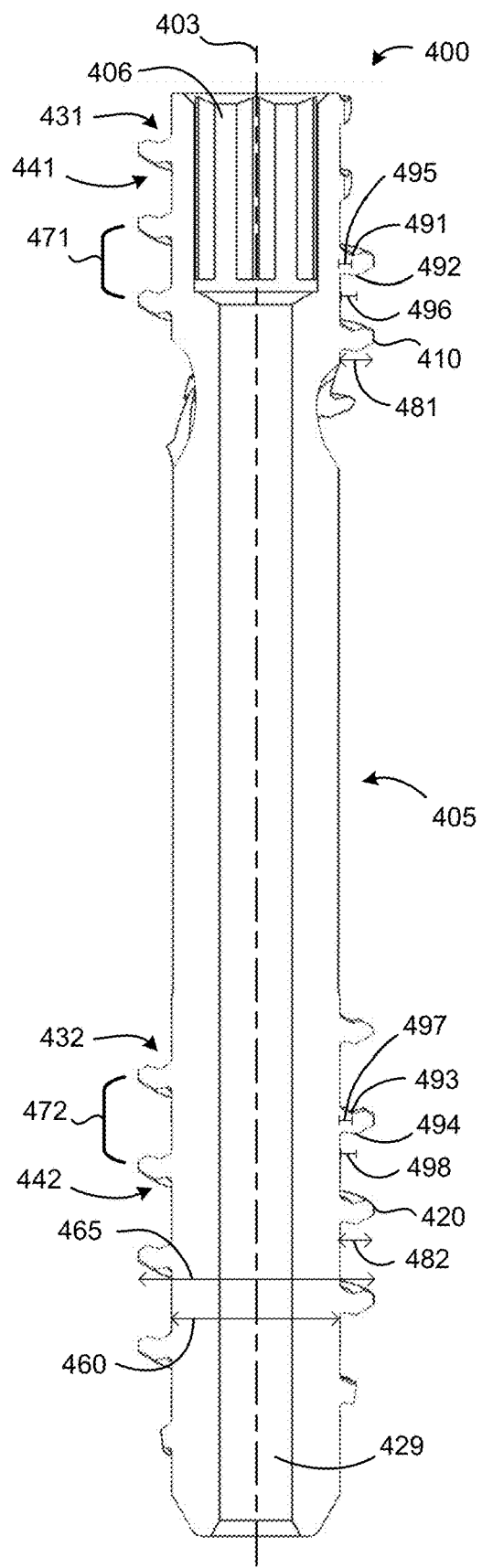
FIG. 4C
FIG. 4D

FASTENING DEVICES, SYSTEMS, AND METHODS

CROSS-REFERENCE TO RELATED APPLICATIONS

This application claims the benefit of U.S. Provisional Patent Application Ser. No. 63/147,640 filed on Feb. 9, 2021, entitled "FASTENING DEVICES, SYSTEMS, AND METHODS". The foregoing document is hereby incorporated by reference in its entirety.

TECHNICAL FIELD

The present disclosure relates to fastening devices, systems, and methods. More specifically, the present disclosure relates to fastening devices with improved thread designs and fastening systems/methods utilizing fastening devices with improved thread designs.

BACKGROUND

Surgical procedures involving fasteners implanted within bone and other tissues can become lose over time due to multi-axial forces and off-axis loading scenarios that may be applied to the fastener during the healing process. Traditional fastener thread designs may not provide sufficient fastener fixation to overcome these multi-axial forces and off-axis loading scenarios.

Accordingly, fasteners with improved thread designs for increasing bone fixation and load sharing between a bone/fastener interface experiencing multi-axial and off-loading conditions would be desirable.

SUMMARY

The various fastening devices, systems, and methods of the present disclosure have been developed in response to the present state of the art, and in particular, in response to the problems and needs in the art that have not yet been fully solved by currently available fastening devices, systems, and methods. In some embodiments, the fastening devices, systems, and methods of the present disclosure may provide improved bone fixation and load sharing between a bone/fastener interface under multi-axial and off-loading conditions.

In some embodiments, a compression fastener may include a shaft and a helical thread disposed about the shaft. The shaft may include a proximal end, a distal end, a proximal shaft portion, and a distal shaft portion. The helical thread may include at least one concave undercut surface and a plurality of pitches that may include at least one first pitch along the proximal shaft portion and at least one second pitch along the distal shaft portion. The at least one concave undercut surface may be angled towards one of the proximal end and the distal end of the shaft. The at least one first pitch and the at least one second pitch may not be equal to each other.

In some embodiments, the shaft may include a smooth shaft portion intermediate the proximal shaft portion and the distal shaft portion.

In some embodiments, the plurality of pitches may include a first discrete pitch along the proximal shaft portion and a second discrete pitch along the distal shaft portion.

In some embodiments, the first discrete pitch may be less than the second discrete pitch.

In some embodiments, the first discrete pitch may be greater than the second discrete pitch.

In some embodiments, the plurality of pitches may include a continuously variable pitch.

In some embodiments, the continuously variable pitch may decrease moving from the distal end of the shaft toward the proximal end of the shaft.

In some embodiments, a compression fastener may include a shaft, a first helical thread, and a second helical thread. The shaft may include a proximal end, a distal end, a proximal shaft portion, a distal shaft portion, and a smooth shaft portion intermediate the proximal shaft portion and the distal shaft portion. The first helical thread may be disposed about the proximal shaft portion and may include a first concave undercut surface, a first pitch, and a first height. The second helical thread may be disposed about the distal shaft portion and may include a second concave undercut surface, a second pitch, and a second height. The first and second concave undercut surfaces may angled towards one of the proximal end and the distal end of the shaft, the first and second pitches may not be equal to each other, and the first and second heights may not be equal to each other.

In some embodiments, the first pitch may be less than the second pitch.

In some embodiments, the first pitch may be greater than the second pitch.

In some embodiments, the first height may be greater than the second height.

In some embodiments, the first concave undercut surface may include a first inflection point at a first inflection point height, the second concave undercut surface may include a second inflection point at a second inflection point height, and the first inflection point height may be equal to the second inflection point height.

In some embodiments, a proximal end of the second helical thread may be timed with a distal end of the first helical thread.

In some embodiments, a bone fastener may include a shaft, a helical thread disposed about the shaft having a concave undercut surface, and one or more cutting flutes formed in the bone fastener. The shaft may include a proximal end, a distal end, a proximal shaft portion, and a distal shaft portion. The concave undercut surface may be angled towards one of the proximal end and the distal end of the shaft, and the one or more cutting flutes may be shaped to urge bone chips in at least one direction along the shaft as the bone fastener is rotated into a bone.

In some embodiments, the one or more cutting flutes may include a first cutting flute formed in the proximal shaft portion and a second cutting flute formed in the distal shaft portion. The first and second cutting flutes may be configured to urge bone chips in a proximal-to-distal direction along the shaft as the bone fastener is rotated into the bone.

In some embodiments, the one or more cutting flutes may include a first cutting flute formed in the proximal shaft portion and a second cutting flute formed in the distal shaft portion. The first and second cutting flutes may be configured to urge bone chips in a distal-to-proximal direction along the shaft as the bone fastener is rotated into the bone.

In some embodiments, the one or more cutting flutes may include a first cutting flute formed in the proximal shaft portion and a second cutting flute formed in the distal shaft portion. The first cutting flute may be configured to urge bone chips in a proximal-to-distal direction along the shaft as the bone fastener is rotated into the bone, and the second cutting flute may be configured to urge bone chips in a distal-to-proximal direction along the shaft as the bone fastener is rotated into the bone.

In some embodiments, the one or more cutting flutes may include a first cutting flute formed in the proximal shaft portion and a second cutting flute formed in the distal shaft portion. The first cutting flute may be configured to urge bone chips in a distal-to-proximal direction along the shaft as the bone fastener is rotated into the bone, and the second cutting flute may be configured to urge bone chips in a proximal-to-distal direction along the shaft as the bone fastener is rotated into the bone.

In some embodiments, the proximal shaft portion may include one or more proximal reverse cutting flutes.

In some embodiments, the distal shaft portion may include one or more distal reverse cutting flutes.

In some embodiments, a method for fabricating a compression fastener may include placing a first cutting tool at a proximal shaft portion of a substantially cylindrical substrate, rotating the substantially cylindrical substrate, and translating the first cutting tool along the proximal shaft portion to form a fourth open surface of a first helical thread disposed about the proximal shaft portion, the first helical thread having a first pitch and a first height. The method may also include placing the first cutting tool at a distal shaft portion of the substantially cylindrical substrate, rotating the substantially cylindrical substrate, and translating the first cutting tool along the distal shaft portion to form a fourth open surface of a second helical thread disposed about the distal shaft portion, the second helical thread having a second pitch and a second height. The method may additionally include placing a second cutting tool at the proximal shaft portion of the substantially cylindrical substrate, rotating the substantially cylindrical substrate, and translating the second cutting tool along the proximal shaft portion to form a first undercut surface and a second undercut surface of the first helical thread. The method may further include placing the second cutting tool at the distal shaft portion of the substantially cylindrical substrate, rotating the substantially cylindrical substrate, and translating the second cutting tool along the distal shaft portion to form a first undercut surface and a second undercut surface of the second helical thread. The method may also include placing a third cutting tool at the proximal shaft portion of the substantially cylindrical substrate, rotating the substantially cylindrical substrate, and translating the third cutting tool along the proximal shaft portion to form a third undercut surface of the first helical thread. The method may additionally include placing the third cutting tool at the distal shaft portion of the substantially cylindrical substrate, rotating the substantially cylindrical substrate, and translating the third cutting tool along the distal shaft portion to form a third undercut surface of the second helical thread. In some embodiments of the method, the first pitch of the first helical thread may not be equal to the second pitch of the second helical thread, and the first height of the first helical thread may not be equal to the second height of the second helical thread.

In some embodiments, the method may also include rotating the substantially cylindrical substrate and translating the first cutting tool along the proximal shaft portion to form a fifth open surface of the first helical thread.

In some embodiments, the method may also include rotating the substantially cylindrical substrate and translating the first cutting tool along the distal shaft portion to form a fifth open surface of the second helical thread.

In some embodiments, the method may also include placing a cutting tool at an intermediate shaft portion of the substantially cylindrical substrate, rotating the substantially cylindrical substrate, and translating the cutting tool along the intermediate shaft portion to form a smooth shaft portion of the substantially cylindrical substrate intermediate the first helical thread and the second helical thread.

In some embodiments, the first undercut surface and the second undercut surface of the first helical thread may comprise a first concave undercut surface, the first undercut surface and the second undercut surface of the second helical thread may comprise a second concave undercut surface, the third undercut surface and the fourth open surface of the first helical thread may comprise a first convex undercut surface, and the third undercut surface and the fourth open surface of the second helical thread may comprise a second convex undercut surface.

In some embodiments, the first and second concave undercut surfaces and the first and second convex undercut surfaces may comprise crescent shapes oriented toward one of a proximal end and a distal end of the substantially cylindrical substrate.

In some embodiments, the first and second concave undercut surfaces and the first and second convex undercut surfaces may comprise chevron shapes oriented toward one of a proximal end and a distal end of the substantially cylindrical substrate.

In some embodiments, the first concave undercut surface may comprise a first inflection point at a first inflection point height, the first convex undercut surface may comprise a second inflection point at a second inflection point height, the second concave undercut surface may comprise a third inflection point at a third inflection point height, and the second convex undercut surface may comprise a fourth inflection point at a fourth inflection point height. The first inflection point height may be equal to the third inflection point height and the second inflection point height may be equal to the fourth inflection point height.

In some embodiments, the first pitch of the first helical thread may be less than the second pitch of the second helical thread.

In some embodiments, the first pitch of the first helical thread may be greater than the second pitch of the second helical thread.

In some embodiments, the first height of the first helical thread may be greater than the second height of the second helical thread.

In some embodiments, the first height of the first helical thread may be less than the second height of the second helical thread.

In some embodiments, a proximal end of the second helical thread may be timed with a distal end of the first helical thread.

In some embodiments, the first pitch of the first helical thread may remain constant irrespective of a selected thickness for the first helical thread.

In some embodiments, the second pitch of the second helical thread may remain constant irrespective of a selected thickness for the second helical thread.

In some embodiments, a method for fabricating a compression fastener may include forming a first helical thread disposed about a proximal shaft portion of a substantially cylindrical substrate and forming a second helical thread disposed about a distal shaft portion of the substantially cylindrical substrate. The first helical thread may include a first inboard portion projecting from the substantially cylindrical substrate at a first height and an outboard portion extending from the first inboard portion, the outboard portion projecting from the substantially cylindrical substrate at a second height that is greater than the first height. The second helical thread may include a second inboard portion projecting from the substantially cylindrical substrate at a third height. The second height of the outboard portion may be greater than the third height of the second inboard portion, and the third height of the second inboard portion may be equal to the first height of the first inboard portion.

In some embodiments of the method, the first inboard portion of the first helical thread may comprise a first shape, and the second inboard portion of the second helical thread may comprise a second shape.

In some embodiments of the method, the first shape and the second shape may be substantially equal to each other.

In some embodiments of the method, the first shape and the second shape may comprise crescent shapes oriented toward one of a proximal end and a distal end of the substantially cylindrical substrate.

In some embodiments of the method, the first shape and the second shape may comprise chevron shapes oriented toward one of a proximal end and a distal end of the substantially cylindrical substrate.

In some embodiments of the method, the first inboard portion may include a first inflection point at a first inflection point height and a second inflection point at a second inflection point height. The second inboard portion may include a third inflection point at a third inflection point height and a fourth inflection point at a fourth inflection point height. The first inflection point height may be equal to the third inflection point height, and the second inflection point height may be equal to the fourth inflection point height.

These and other features and advantages of the present disclosure will become more fully apparent from the following description and appended claims or may be learned by the practice of the devices, systems, and methods set forth hereinafter.

BRIEF DESCRIPTION OF THE DRAWINGS

Exemplary embodiments of the present disclosure will become more fully apparent from the following description taken in conjunction with the accompanying drawings. Understanding that these drawings depict only exemplary embodiments and are, therefore, not to be considered limiting of the scope of the present disclosure, the exemplary embodiments of the present disclosure will be described with additional specificity and detail through use of the accompanying drawings in which:

FIG. 1C illustrates a side view of the fastener of FIG. 1A; FIG. 1D illustrates a cross-sectional side view of the fastener of FIG. 1A taken along the line A-A shown in FIG. 1C;

FIG. 4C illustrates a side view of the fastener of FIG. 4A; FIG. 4D illustrates a cross-sectional side view of the fastener of FIG. 4A taken along the line B-B shown in FIG. 4C;

Figure 1A:
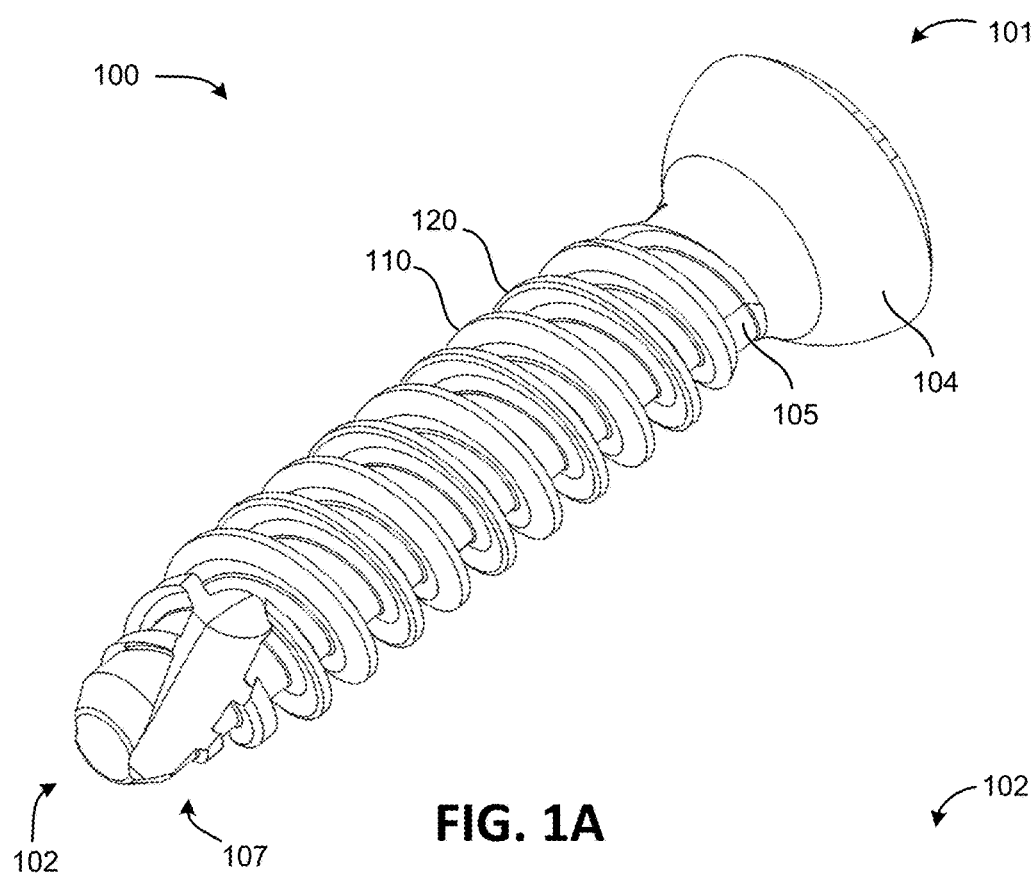
FIG. 1A illustrates a front perspective view of a fastener, according to an embodiment of the present disclosure.

It is to be understood that the drawings are for purposes of illustrating the concepts of the present disclosure and may not be drawn to scale. Furthermore, the drawings illustrate exemplary embodiments and do not represent limitations to the scope of the present disclosure.

DETAILED DESCRIPTION

Exemplary embodiments of the present disclosure will be best understood by reference to the drawings, wherein like parts are designated by like numerals throughout. It will be readily understood that the components of the present disclosure, as generally described and illustrated in the drawings, could be arranged, and designed in a wide variety of different configurations. Thus, the following more detailed description of the embodiments of the implants, systems, and methods, as represented in the drawings, is not intended to limit the scope of the present disclosure but is merely representative of exemplary embodiments of the present disclosure.

The word "exemplary" is used herein to mean "serving as an example, instance, or illustration." Any embodiment described herein as "exemplary" is not necessarily to be construed as preferred or advantageous over other embodiments. While the various aspects of the embodiments are presented in the drawings, the drawings are not necessarily drawn to scale unless specifically indicated.

Figure 1B:
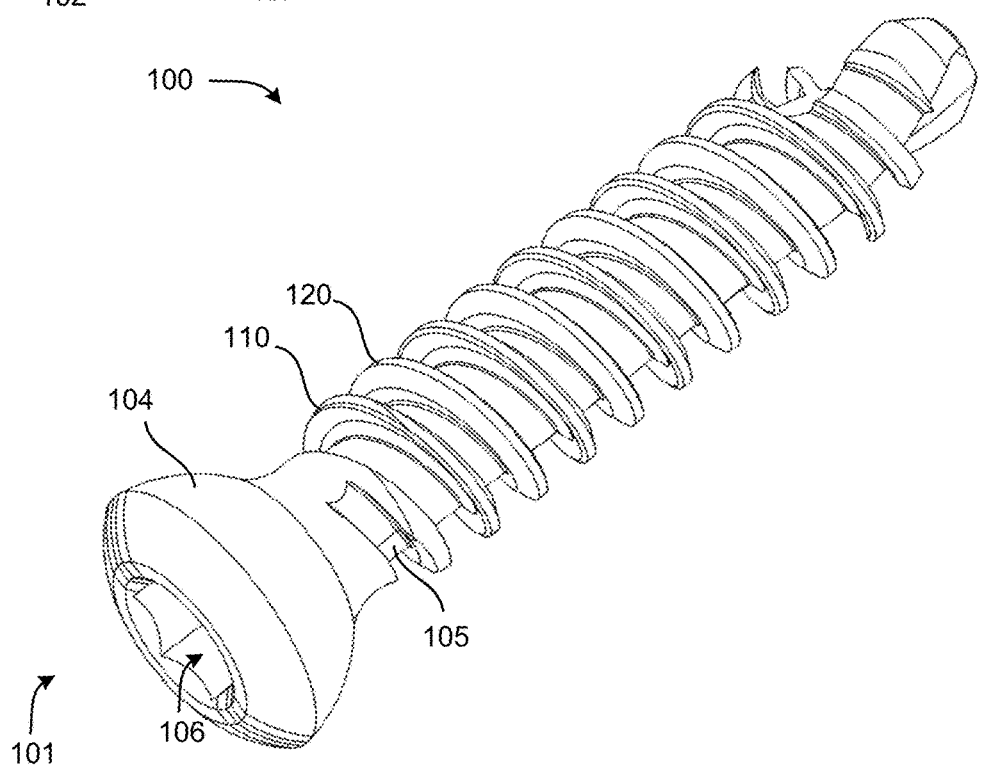
FIG. 1B illustrates a rear perspective view of the fastener of FIG. 1A.

FIGS. 1A-1D illustrate various views of a fastener 100, implantable bone anchor, or bone screw, according to one embodiment of the present disclosure. Specifically, FIG. 1A is a front perspective view of the fastener 100, FIG. 1B is a rear perspective view of the fastener 100, FIG. 1C is a side view of the fastener 100, and FIG. 1D is a cross-sectional side view of the fastener 100 taken along the line A-A in FIG. 1C.

In general, the fastener 100 may include a shaft 105 having a proximal end 101, a distal end 102, and a longitudinal axis 103. The fastener 100 may also include a head 104 located at the proximal end 101 of the shaft 105, a torque connection interface 106 formed in/on the head 104 (in either a male/female configuration), and a self-tapping feature 107 formed in the distal end 102 of the shaft 105.

In some embodiments, the fastener 100 may include a first helical thread 110 disposed about the shaft 105, and a second helical thread 120 disposed about the shaft 105 adjacent the first helical thread 110.

In some embodiments, the fastener 100 may include a "dual start" or "dual lead" thread configuration comprising the first helical thread 110 and the second helical thread 120.

In some embodiments, a depth of the first helical thread 110 and/or the second helical thread 120 with respect to the shaft 105 may define a major diameter vs. a minor diameter of the shaft 105 alone.

In some embodiments, a major diameter and/or a minor diameter of the fastener 100 may be constant or substantially constant along the entire length of the fastener, or along a majority of the length of the fastener. In these embodiments, a constant minor diameter may help avoid blowout of narrow/delicate bones (e.g., a pedicle) when inserting a fastener into a bone. In some embodiments, a pilot hole may first be drilled into a narrow/delicate bone and then a fastener having a similar minor diameter in comparison to the diameter of the pilot hole may be chosen to avoid blowout when inserting the fastener into the bone, as will be discussed in more detail below.

In some embodiments, a depth of the first helical thread 110 and/or the second helical thread 120 with respect to the shaft 105 may vary along a length of the shaft 105 to define one or more major diameters of the fastener 100 and/or one or more regions along the fastener 100 may comprise one or more continuously variable major diameters.

In some embodiments, a thickness of the shaft 105 may vary along a length of the shaft 105 to define one or more minor diameters of the fastener 100, and/or one or more regions along the fastener 100 may comprise one or more continuously variable minor diameters.

In some embodiments, a thickness/height/width/length/pitch/angle/shape, etc., of the first helical thread 110 and/or the second helical thread 120 (or any additional helical thread) may vary along a length of the shaft 105. For example, a thickness/height/width/length/pitch/angle/shape, etc., of the first helical thread 110 and/or the second helical thread 120 may be greater towards the tip of the fastener and thinner towards the head of the fastener (or vice versa) in either a discrete or continuously variable fashion, etc.

In some embodiments, the major and/or minor diameters may increase toward a proximal end or head of a fastener in order to increase bone compaction as the fastener is terminally inserted into the bone/tissue.

In some embodiments, a pitch of the first helical thread 110 and/or the second helical thread 120 may vary along a length of the fastener 100.

In some embodiments, the fastener 100 may include a plurality of helical threads disposed about the shaft 105. However, it will also be understood that any of the fasteners disclosed or contemplated herein may include a single helical thread disposed about the shaft of the fastener. Moreover, the fastener 100 may comprise a nested plurality of helical threads having different lengths (not shown). As one non-limiting example, the fastener 100 may include a first helical thread 110 that is longer than a second helical thread 120, such that the fastener 100 comprises dual threading along a first portion of the shaft 105 and single threading along a second portion of the shaft 105.

In some embodiments, the plurality of helical threads may include three helical threads comprising a "triple start" or "triple lead" thread configuration (not shown).

In some embodiments, the plurality of helical threads may include four helical threads comprising a "quadruple start" or "quadruple lead" thread configuration (not shown).

In some embodiments, the plurality of helical threads may include more than four helical threads (not shown).

In some embodiments, the fastener 100 may include first threading with any of the shapes disclosed herein oriented toward one of the proximal end and the distal end of the fastener 100, with the first threading located proximate the distal end of the fastener 100, as well as second threading with any of the shapes disclosed herein oriented toward the other one of the proximal end and the distal end of the fastener 100, with the second threading located proximate the head of the fastener 100 (not shown).

In some embodiments, the fastener 100 may include multiple threading (e.g., dual helical threading, etc.) with any of the shapes disclosed herein located proximate one of the proximal end and the distal end of the fastener 100, as well as single threading with any of the shapes disclosed herein with the second threading located proximate the other of the proximal end and the distal end of the fastener 100.

In some embodiments, the first helical thread 110 may include a plurality of first concave undercut surfaces 131 and a plurality of first convex undercut surfaces 141.

In some embodiments, the second helical thread 120 may include a plurality of second concave undercut surfaces 132 and a plurality of second convex undercut surfaces 142.

In some embodiments, when the fastener 100 is viewed in section along a plane that intersects the longitudinal axis 103 of the shaft 105 (e.g., see FIG. 1D), the plurality of first concave undercut surfaces 131 and the plurality of second convex undercut surfaces 142 may be oriented toward (i.e., point toward) the proximal end 101 of the shaft 105.

In some embodiments, the plurality of first convex undercut surfaces 141 and the plurality of second concave undercut surfaces 132 may be oriented toward (i.e., point toward) the distal end 102 of the shaft 105.

In some embodiments, at least one of the plurality of first concave undercut surfaces 131, the plurality of first convex undercut surfaces 141, the plurality of second concave undercut surfaces 132, and the plurality of second convex undercut surfaces 142 may comprise at least one substantially flat surface.

In some embodiments, when the fastener 100 is viewed in section along a plane intersecting the longitudinal axis 103 of the shaft 105, the first helical thread 110 may comprise a plurality of first bent shapes (comprising at least one surface that is angled relative to the longitudinal axis 103 of the shaft 105 and/or at least one undercut surface) with a plurality of first intermediate portions 151 that are oriented toward (i.e., point toward) the distal end 102 of the shaft 105. This may be referred to as "standard" threading, having a "standard" orientation.

In some embodiments, when the fastener 100 is viewed in section along a plane intersecting the longitudinal axis 103 of the shaft 105, the second helical thread 120 may comprise a plurality of second bent shapes (comprising at least one surface that is angled relative to the longitudinal axis 103 of the shaft 105 and/or at least one undercut surface) with a plurality of second intermediate portions 152 that are oriented toward (i.e., point toward) the proximal end 101 of the shaft 105. This may be referred to as "inverted" threading, having an "inverted" orientation.

In some embodiments, one or more helical threads may morph/transition between a standard orientation and an inverted orientation along a shaft of a fastener.

In some embodiments, at least one of the plurality of first concave undercut surfaces 131, the plurality of first convex undercut surfaces 141, the plurality of second concave undercut surfaces 132, and the plurality of second convex undercut surfaces 142 may comprise at least one curved surface.

As shown in FIG. 1D, the proximally-oriented and distally-oriented surfaces of the first helical thread 110 (i.e., the first concave undercut surfaces 131 and the first convex undercut surfaces 141 in the fastener 100 of FIG. 1D) may not have mirror symmetry relative to each other about any plane perpendicular to the longitudinal axis 103 of the fastener 100. Rather, the first concave undercut surfaces 131 and the first convex undercut surfaces 141 may be generally parallel to each other. The same may be true for the second helical thread 120, in which the second concave undercut surfaces 132 and the second convex undercut surfaces 142 may not have mirror symmetry relative to each other but may be generally parallel to each other.

Conversely, as also shown in FIG. 1D, the proximally-oriented surfaces of the first helical thread 110 may have mirror symmetry relative to the distally-oriented surfaces of the second helical thread 120. Specifically, the first concave undercut surfaces 131 may have mirror symmetry relative to the second convex undercut surfaces 142 about a plane 170 that bisects the space between them and lies perpendicular to the longitudinal axis 103.

Similarly, the distally-oriented surfaces of the first helical thread 110 may have mirror symmetry relative to the proximally-oriented surfaces of the second helical thread 120. Specifically, the second concave undercut surfaces 132 may have mirror symmetry relative to the first convex undercut surfaces 141 about a plane 172 that bisects the space between them and lies perpendicular to the longitudinal axis 103.

This mirror symmetry may be present along most of the length of the first helical thread 110 and the second helical thread 120, with symmetry across different planes arranged between adjacent turns of the first helical thread 110 and the second helical thread 120 along the length of the longitudinal axis 103. Such mirror symmetry may help more effectively capture bone between the first helical thread 110 and the second helical thread 120 and may also facilitate manufacture of the fastener 100.

Figure 2:
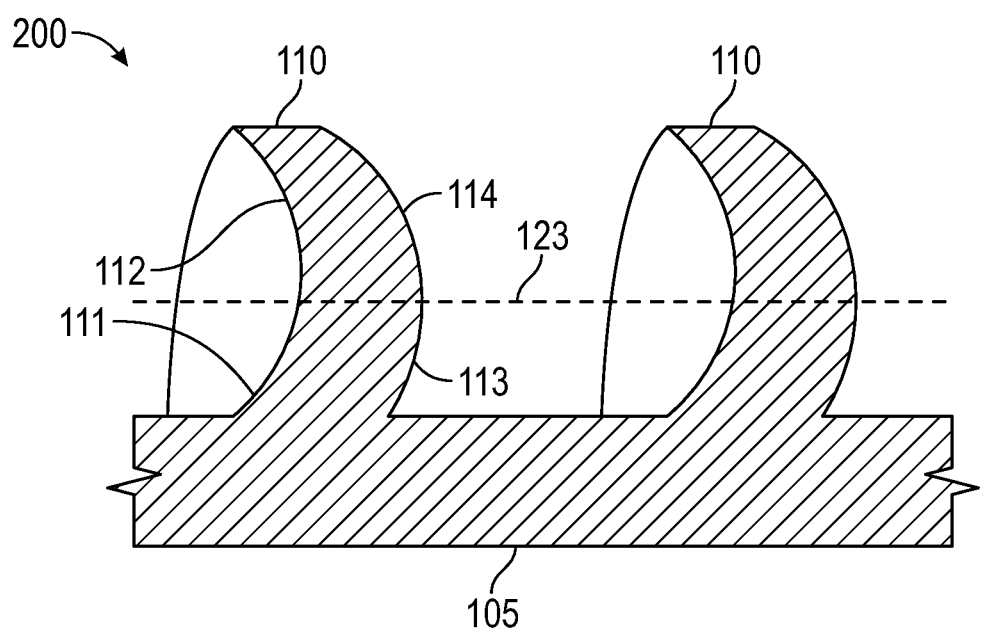
FIG. 2 illustrates a partial cross-sectional side view of a fastener comprising crescent-shaped threading.

In some embodiments, when the fastener 100 is viewed in section along a plane intersecting the longitudinal axis 103 of the shaft 105, the first helical thread 110 may include at least one partial crescent shape that is oriented toward (i.e., points toward) the distal end 102 of the shaft 105 and/or the proximal end 101 of the shaft 105. FIG. 2 illustrates a partial cross-sectional view of a fastener 200 comprising crescent shapes, as one non-limiting example of such an embodiment.

In some embodiments (not shown), when the fastener 100 is viewed in section along a plane intersecting the longitudinal axis 103 of the shaft 105, the first helical thread 110 may include at least one partial crescent shape that is oriented toward (i.e., points toward) the distal end 102 of the shaft 105, and the second helical thread 120 may include at least one partial crescent shape that is oriented toward (i.e., points toward) the proximal end 101 of the shaft 105.

In some embodiments (not shown), the first helical thread 110 may include a first plurality of partial crescent shapes that are oriented toward (i.e., point toward) the distal end 102 of the shaft 105, and the second helical thread 120 may include a second plurality of partial crescent shapes that are oriented toward (i.e., point toward) the proximal end 101 of the shaft 105.

In some embodiments (not shown), the first plurality of partial crescent shapes and the second plurality of partial crescent shapes may be arranged in alternating succession along the shaft 105 of the fastener 100.

In some embodiments, the first helical thread 110 may be bisected by the line 123 shown in FIG. 2 with each crescent shape including a plurality of first undercut surfaces 111, a plurality of second undercut surfaces 112, a plurality of third undercut surfaces 113, and a plurality of fourth open surfaces 114 similar to the helical threading shown in FIG. 1D, except with curved surfaces in place of flat surfaces.

In some embodiments, the plurality of first undercut surfaces 111 and the plurality of second undercut surfaces 112 may comprise concave curved surfaces. However, it will be understood that portions of the plurality of first undercut surfaces 111 and/or portions of the plurality of second undercut surfaces 112 may also comprise convex curved surfaces and/or flat surfaces (not shown in FIG. 2).

In some embodiments, the plurality of third undercut surfaces 113 and the plurality of fourth open surfaces 114 may comprise convex curved surfaces. However, it will be understood that portions of the plurality of third undercut surfaces 113 and the plurality of fourth open surfaces 114 may also comprise concave curved surfaces and/or flat surfaces (not shown in FIG. 2).

In some embodiments, the plurality of third undercut surfaces 113 and the plurality of fourth open surfaces 114 may be replaced by a ramped surface (such as that utilized in a standard buttress thread design) without any undercuts (not shown in FIG. 2). Likewise, any of the other thread designs disclosed herein may utilize a ramped or buttress thread design on at least one side of the helical thread.

In some embodiments, a fastener may have only standard threads or only inverted threads. The type of threads that are desired may depend on the type and/or magnitude of loads to be applied to the fastener. For example, a screw loaded axially away from the bone in which it is implanted may advantageously have a standard thread, while a screw loaded axially toward the bone in which it is implanted may advantageously have an inverted thread. A screw that may experience multi-axial loading and/or off-loading conditions may advantageously include at least one standard thread and at least one inverted thread in order to increase bone fixation and load sharing between a bone/fastener interface during multi-axial and off-loading conditions to reduce high bone strain and distribute multi-axial forces applied to the bone in a load-sharing, rather than load-bearing, configuration. Shear loads and/or bending moments may also be optimally resisted with any chosen combination of threading, threading morphology, and/or threading variations contemplated herein to optimally resist shear loads, bending moments, multi-axial loading, off-loading conditions, etc.

In some embodiments, fasteners with standard threads may be used in conjunction with fasteners with inverted threads in order to accommodate different loading patterns.

In some embodiments, a single fastener may have both standard and inverted threads, like the fastener 100. Such a combination of threads may help the fastener 100 remain in place with unknown and/or varying loading patterns.

In some embodiments, the geometry of the threading of a fastener (with standard and/or inverted threads) may be varied to suit the fastener for a particular loading scheme. For example, the number of threads, the number of thread starts, the pitch of the threading, the lead(s) of the threading, the shape(s) of the threading, any dimension(s) associated with the threading (e.g., any length(s)/width(s)/height(s)/inflection point(s), etc., associated with the threading), the major diameter(s), the minor diameter(s), any angulation/angles associated with any surfaces of the threading, the "handedness" of the threading (e.g., right-handed vs. left-handed), etc., may be varied accordingly to suit any specific medium of installation, loading pattern, desired radial loading force, pull-out strength, application, procedure, etc., that may be involved.

In some embodiments, the material(s) of any portion of a fastener described herein may include, but are not limited to metals (e.g., titanium, cobalt, stainless steel, etc.), metal alloys, plastics, polymers, ceramics, PEEK, UHMWPE, composites, additive particles, textured surfaces, biologics, biomaterials, bone, etc.

In some embodiments, any of the fasteners described herein may include additional features such as: self-tapping features, locking features (e.g., locking threading formed on a portion of the fastener, such as threading located on or near a head of the fastener), cannulation, any style of fastener head (or no fastener head at all), any style of torque connection interface (or no torque connection interface at all), etc.

In some embodiments, a tap (not shown) may be utilized to pre-form threading in a bone according to any threading shape that is disclosed or contemplated herein. In this manner, taps with any suitable shape may be utilized in conjunction with any fastener described or contemplated herein to match or substantially match the threading geometry of a given fastener.

In some embodiments, a minor diameter of the fastener may be selected to match, or substantially match, a diameter of a pilot hole that is formed in a bone to avoid bone blowout when the fastener is inserted into the pilot hole.

Additionally, or alternatively thereto, the type of threads and/or thread geometry may be varied based on the type of bone in which the fastener is to be anchored. For example, fasteners anchored in osteoporotic bone may fare better with standard or inverted threads, or when the pitch, major diameter, and/or minor diameter are increased or decreased, or when the angulation of thread surfaces is adjusted, etc.

In some embodiments, a surgical kit may include multiple fasteners with any of the different fasteners and thread options described or contemplated herein. The surgeon may select the appropriate fastener(s) from the kit based on the particular loads to be applied and/or the quality of bone in which the fastener(s) are to be anchored.

Continuing with FIG. 1D, in some embodiments the first helical thread 110 may include a plurality of first undercut surfaces 111, a plurality of second undercut surfaces 112, a plurality of third undercut surfaces 113, and a plurality of fourth open surfaces 114.

In some embodiments, the second helical thread 120 may include a plurality of fifth undercut surfaces 125, a plurality of sixth undercut surfaces 126, a plurality of seventh undercut surfaces 127, and a plurality of eighth open surfaces 128.

In some embodiments, one or more of the plurality of first undercut surfaces 111, the plurality of second undercut surfaces 112, the plurality of third undercut surfaces 113, the plurality of fourth open surfaces 114, the plurality of fifth undercut surfaces 125, the plurality of sixth undercut surfaces 126, the plurality of seventh undercut surfaces 127, and the plurality of eighth open surfaces 128 may comprise at least one flat or substantially flat surface.

In some embodiments, the plurality of first undercut surfaces 111, the plurality of third undercut surfaces 113, the plurality of sixth undercut surfaces 126, and the plurality of eighth open surfaces 128 may be angled towards the distal end 102 of the shaft 105.

In some embodiments, the plurality of second undercut surfaces 112, the plurality of fourth open surfaces 114, the plurality of fifth undercut surfaces 125, and the plurality of seventh undercut surfaces 127 may be angled towards the proximal end 101 of the shaft 105.

In some embodiments, when the fastener 100 is viewed in section along a plane that intersects the longitudinal axis 103 of the shaft 105 (as shown in FIG. 1D), the first helical thread 110 may include at least one chevron shape that is oriented toward (i.e., points toward) the distal end 102 of the shaft 105. Likewise, the second helical thread 120 may also include at least one chevron shape that is oriented toward (i.e., points toward) the proximal end 101 of the shaft 105.

In some embodiments, when the fastener 100 is viewed in section along a plane that intersects the longitudinal axis 103 of the shaft 105 (as shown in FIG. 1D), the first helical thread 110 may include a first plurality of chevron shapes that are oriented toward (i.e., point toward) the distal end 102 of the shaft 105. Likewise, the second helical thread 120 may include a second plurality of chevron shapes that are oriented toward (i.e., point toward) the proximal end 101 of the shaft 105.

In some embodiments, the first plurality of chevron shapes and the second plurality of chevron shapes may be arranged in alternating succession along the shaft 105 of the fastener 100, (e.g., see FIG. 1D).

In some embodiments, a plurality of first interlocking spaces 161 and a plurality of second interlocking spaces 162 may be formed between the first helical thread 110 and the second helical thread 120 along the shaft 105 of the fastener 100.

In some embodiments, the plurality of first interlocking spaces 161 may be formed intermediate the first concave undercut surfaces 131 and the second concave undercut surfaces 132.

In some embodiments, the plurality of second interlocking spaces 162 may be formed intermediate the first convex undercut surfaces 141 and the second convex undercut surfaces 142.

In some embodiments, the plurality of first interlocking spaces 161 may be larger in size than the plurality of second interlocking spaces.

In some embodiments, the plurality of first interlocking spaces 161 and the plurality of second interlocking spaces 162 may be shaped and/or configured to interlock with bone/other tissues received therein to increase fixation of the fastener 100 within the bone/other tissues and provide additional resistance against multi-axial forces that may be applied to the fastener 100 and/or the bone/other tissues.

In some embodiments, the plurality of second undercut surfaces 112 and the plurality of sixth undercut surfaces 126 may be angled toward each other to trap bone/other tissues within the plurality of first interlocking spaces 161 in order to increase fixation and resistance against multi-axial forces.

In some embodiments, the plurality of third undercut surfaces 113 and the plurality of seventh undercut surfaces 127 may be angled toward each other to trap bone/other tissues within the plurality of second interlocking spaces 162 in order to increase fixation and resistance against multi-axial forces.

In some embodiments, the plurality of first undercut surfaces 111 and the plurality of fifth undercut surfaces 125 may each form an angle $\alpha$ with respect to the longitudinal axis 103 of the shaft 105, as shown in FIG. 1D.

In some embodiments, the angle $\alpha$ may be greater than 90 degrees.

In some embodiments, the plurality of second undercut surfaces 112 and the plurality of sixth undercut surfaces 126 may each form an angle $\beta$ with respect to the longitudinal axis 103 of the shaft 105.

In some embodiments, the angle β may be less than 90 degrees.

In some embodiments, the plurality of third undercut surfaces 113 and the plurality of seventh undercut surfaces 127 may each form an angle θ with respect to the longitudinal axis 103 of the shaft 105.

In some embodiments, the angle θ may be approximately 90 degrees.

In some embodiments, the angle θ may be greater than 90 degrees.

It will be understood that any fastener described or contemplated herein may include any thread configuration, feature, or morphology described or contemplated herein to achieve optimal fixation within a given bone/tissue. Moreover, it will also be understood that any fastener described or contemplated herein may be utilized in conjunction with (or within) any system, method, or instrumentation described or contemplated herein.

Figure 3A:
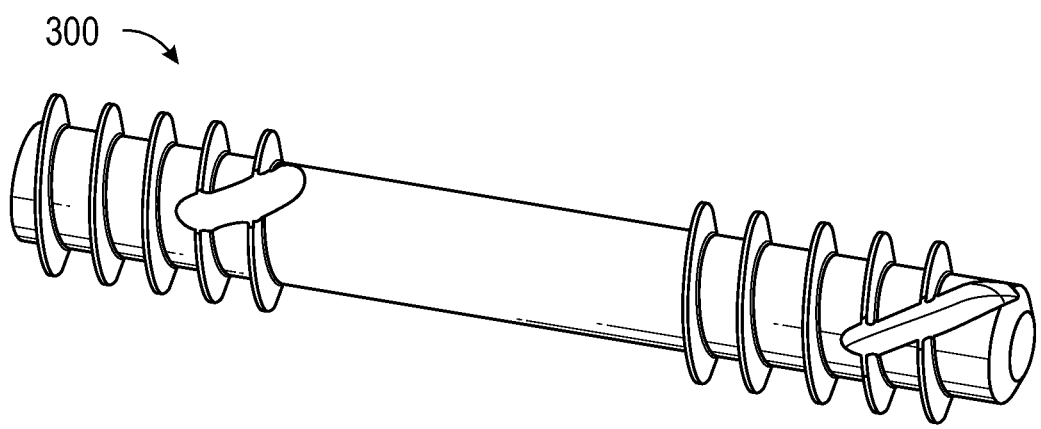
FIG. 3A illustrates a perspective side view of a fastener, according to another embodiment of the present disclosure.

FIG. 3A illustrates a fastener or compression fastener 300, according to another embodiment of the present disclosure, which is discussed below in more detail below with respect to FIGS. 4A-6D. The compression fastener 300 may be utilized to repair bone fractures by compressing two or more bone fragments together to reduce one or more bone fractures. The compression fastener 300 may comprise any thread configuration, feature, or morphology that is described or contemplated herein to achieve optimal fixation within a given bone/tissue.

Figure 3B:
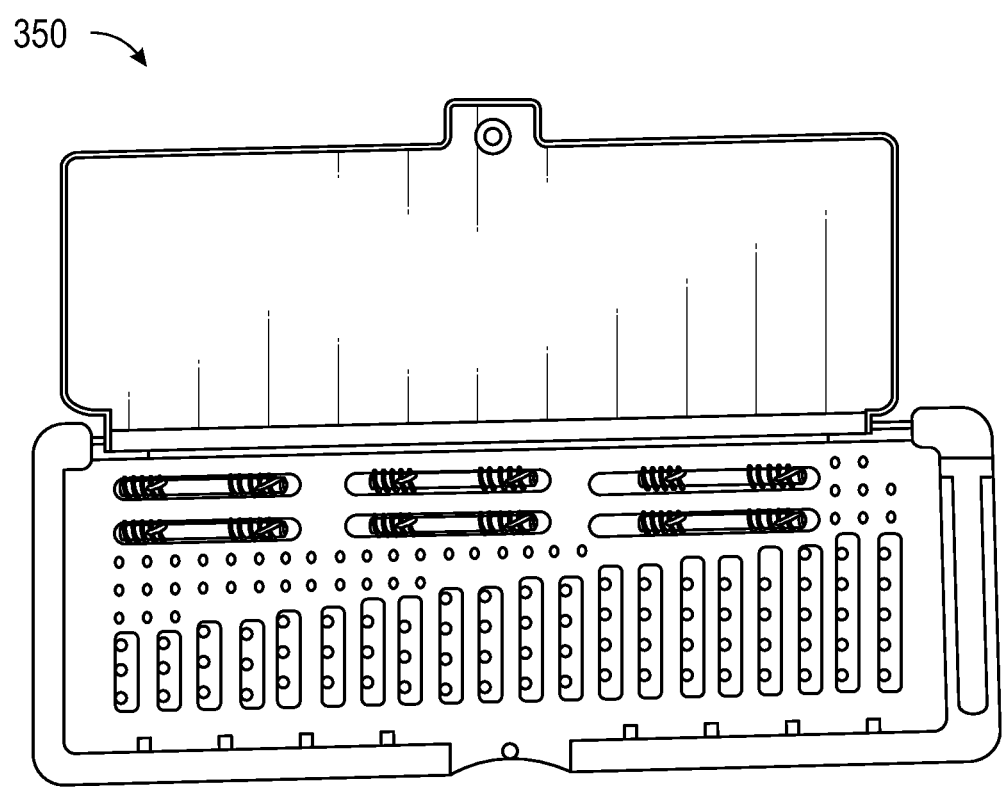
FIG. 3B illustrates a kit comprising the fastener of FIG. 3A.

FIG. 3B illustrates a system/kit 350 that may comprise one or more fasteners that are described or contemplated herein of varying size, morphology, etc., as well as any suitable supporting instruments to help prepare a bone and/or insert a fastener into the bone, etc.

Figure 4A:
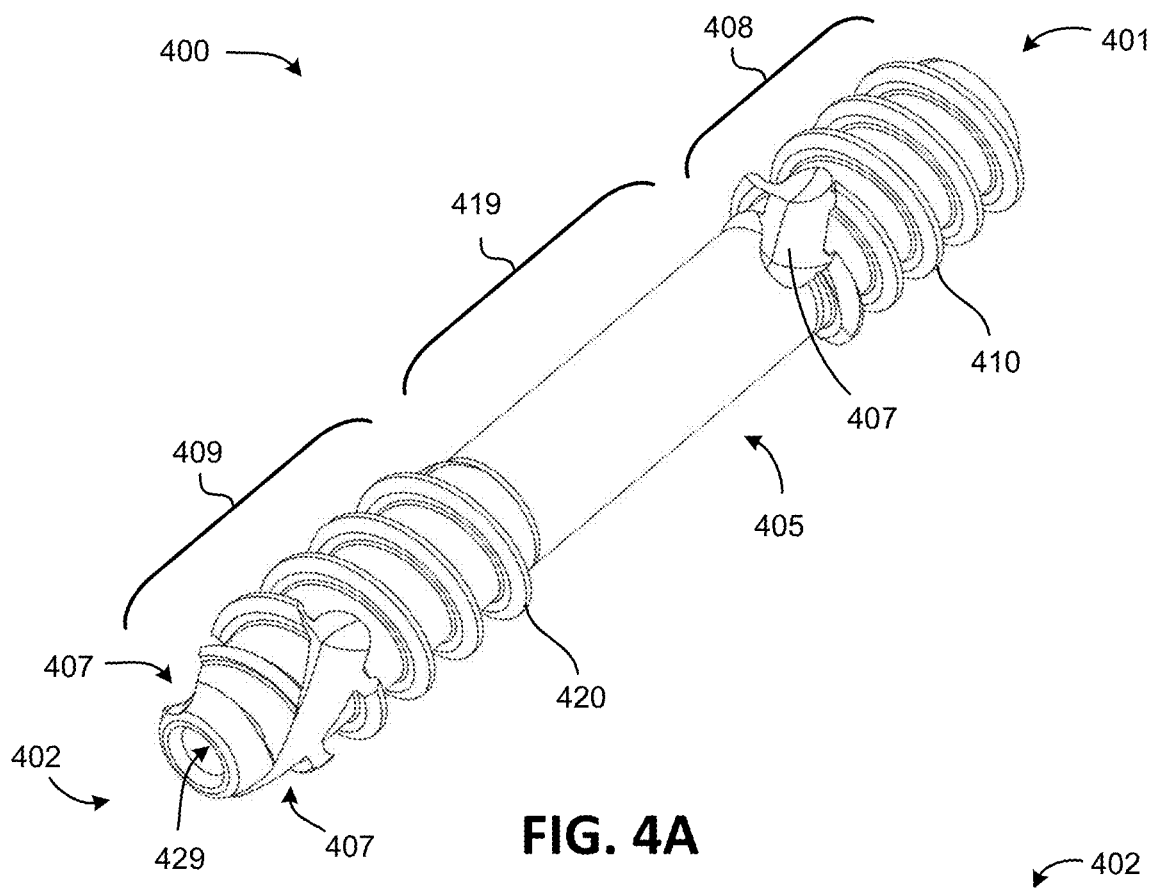
FIG. 4A illustrates a front perspective view of a fastener, according to an embodiment of the present disclosure.
Figure 4B:
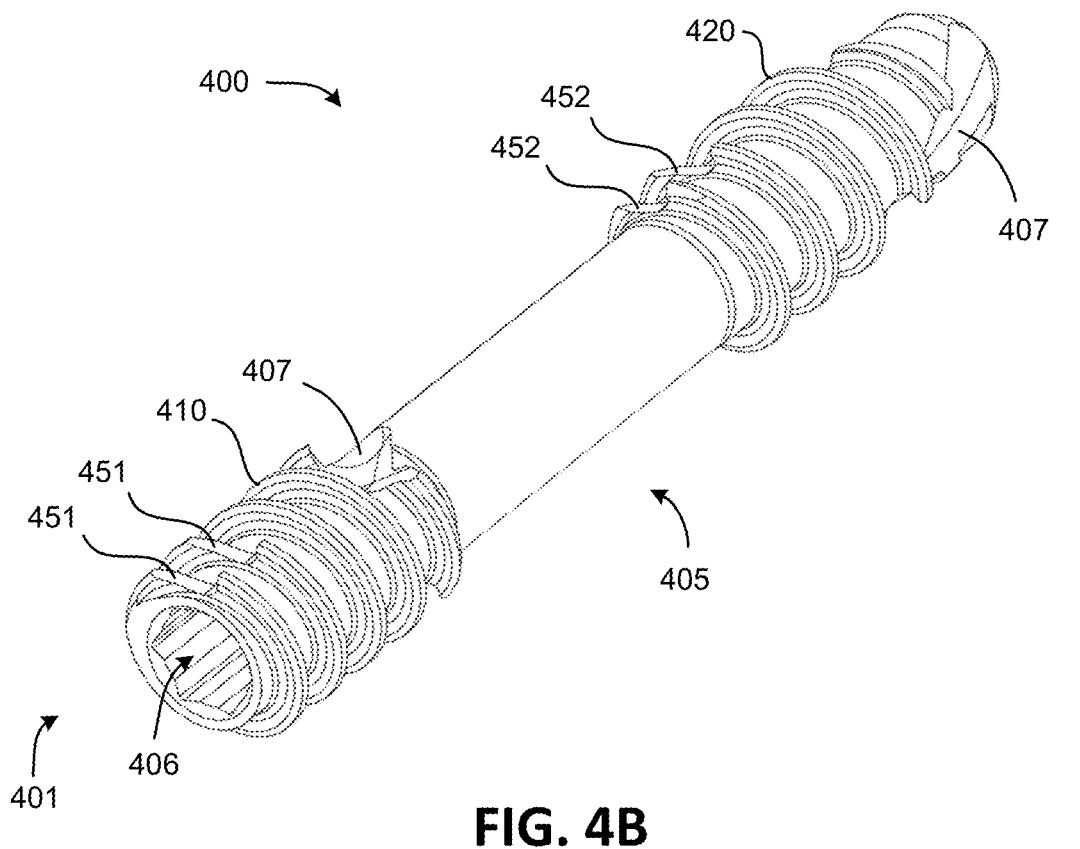
FIG. 4B illustrates a rear perspective view of the fastener of FIG. 4A.

FIGS. 4A-4D illustrate various views of a compression fastener, bone fastener, or fastener 400, according to another embodiment of the present disclosure. Specifically, FIG. 4A is a front perspective view of the fastener 400, FIG. 4B is a rear perspective view of the fastener 400, FIG. 4C is a side view of the fastener 400, and FIG. 4D is a cross-sectional side view of the fastener 400 taken along the line B-B in FIG. 4C.

The fastener 400 may generally include a shaft 405 having a proximal end 401, a distal end 402, a longitudinal axis 403, a proximal shaft portion 408, a distal shaft portion 409, an intermediate shaft portion 419, a first helical thread 410, a second helical thread 420, one or more cutting flutes 407 (and/or reverse cutting flutes), a central longitudinal passageway 429 to enable guided insertion of the fastener 400 over a K-wire or pin (not shown), and a torque connection interface 406.

In some embodiments, the fastener 400 may have a minor diameter 460 defined by the shaft 405 of the fastener 400.

In some embodiments, at least a portion of the minor diameter 460 may be constant along the shaft 405 of the fastener 400.

In some embodiments, at least a portion of the minor diameter 460 may vary along the shaft 405 of the fastener 400.

In some embodiments, the minor diameter of the distal shaft portion 409, the intermediate shaft portion 419, and/or the proximal shaft portion 408 may be constant and/or substantially equal to each other.

In some embodiments, at least a portion of the minor diameter 460 of the distal shaft portion 409 may be smaller than the minor diameter of the intermediate shaft portion 419 and/or the proximal shaft portion 408.

In some embodiments, the fastener 400 may have a major diameter 465 defined by one or more helical threads disposed about the shaft 405 of the fastener 400.

In some embodiments, the one or more helical threads may be disposed about the shaft 405 or portions of the shaft 405, as previously discussed.

In some embodiments, the fastener 400 may include a first helical thread 410 and a second helical thread 420 separated by a smooth shaft portion or intermediate shaft portion 419, as shown in FIGS. 4A-6D.

In some embodiments, the fastener 400 may include a single helical thread disposed about the shaft 405 between the proximal and distal ends 401, 402 of the shaft 405 (not shown). In these embodiments, the single helical thread may span the distal shaft portion 409, the intermediate shaft portion 419, and the proximal shaft portion 408. In these embodiments, the intermediate shaft portion 419 may not be threadless/smooth.

In some embodiments, the fastener 400 may include multiple helical threads disposed about the shaft 405 between the proximal and distal ends 401, 402 of the shaft 405 (not shown). In these embodiments, some or all of the helical threads may span the distal shaft portion 409, the intermediate shaft portion 419, and/or the proximal shaft portion 408. In these embodiments, the intermediate shaft portion 419 may not be threadless/smooth.

In some embodiments, at least a portion of the major diameter 465 may be constant along the one or more helical threads of the fastener 400.

In some embodiments, at least a portion of the major diameter 465 may vary along the one or more helical threads of the fastener 400.

In some embodiments, the major diameter 465 of the one or more helical threads about the distal shaft portion 409, the intermediate shaft portion 419, and/or the proximal shaft portion 408 may be constant and/or substantially equal to each other.

In some embodiments, the major diameter 465 of the one or more helical threads about the distal shaft portion 409, the intermediate shaft portion 419, and/or the proximal shaft portion 408 may not be constant and/or not substantially equal to each other.

In some embodiments, the major diameter 465 of the one or more helical threads about the distal shaft portion 409, the intermediate shaft portion 419, and/or the proximal shaft portion 408 may be continuously variable.

In some embodiments, the major diameter 465 of the one or more helical threads may increase in a continuously variable manner from the distal end 402 of the shaft 405 toward the proximal end 401 of the shaft 405.

In some embodiments, the major diameter 465 of the one or more helical threads may decrease in a continuously variable manner from the distal end 402 of the shaft 405 toward the proximal end 401 of the shaft 405.

In some embodiments, the major diameter 465 of the one or more helical threads may decrease in a continuously variable manner from the distal end 402 of the shaft 405 toward the intermediate shaft portion 419, then increase in a continuously variable manner from the intermediate shaft portion 419 toward the proximal end 401 of the shaft 405.

In some embodiments, the major diameter 465 of the one or more helical threads may increase in a continuously variable manner from the distal end 402 of the shaft 405 toward the intermediate shaft portion 419, then decrease in a continuously variable manner from the intermediate shaft portion 419 toward the proximal end 401 of the shaft 405.

In some embodiments, the major diameter 465 or first height 481 of the first helical thread 410 disposed about the proximal shaft portion 408 may be equal to the major diameter 465 or second height 482 of the second helical thread 420 disposed about the distal shaft portion 409.

In some embodiments, the major diameter 465 or first height 481 of the first helical thread 410 disposed about the proximal shaft portion 408 may not be equal to the major diameter 465 or second height 482 of the second helical thread 420 disposed about the distal shaft portion 409.

In some embodiments, the major diameter 465 or first height 481 of the first helical thread 410 disposed about the proximal shaft portion 408 may be greater than the major diameter 465 or second height 482 of the second helical thread 420 disposed about the distal shaft portion 409. This may allow for greater bone purchase by the first helical thread 410.

However, it will also be understood that in some embodiments the major diameter 465 or first height 481 of the first helical thread 410 disposed about the proximal shaft portion 408 may be less than the major diameter 465 or second height 482 of the second helical thread 420 disposed about the distal shaft portion 409.

In some embodiments, the one or more helical threads disposed about the shaft 405 may include at least one concave undercut surface. The at least one concave undercut surface may be angled towards one of the proximal end 401 and the distal end 402 of the shaft 405.

In some embodiments, the first helical thread 410 may include a first concave undercut surface 431 and the second helical thread 420 may include a second concave undercut surface 432. The first and second concave undercut surfaces 431, 432 may be angled towards one of the proximal end 401 and the distal end 402 of the shaft 405.

However, it will also be understood that the fastener 400 may include any thread configuration, feature, size, morphology, etc., that is described or contemplated herein to achieve optimal fixation within a given bone/tissue. For example, in some embodiments the one or more helical threads may comprise standard or inverted threading (or combinations thereof), a "dual start" thread configuration, crescent shapes, chevron shapes, etc.

In some embodiments, the one or more helical threads may include a plurality of pitches.

In some embodiments, the plurality of pitches may include at least one first pitch along the proximal shaft portion 408, and at least one second pitch along the distal shaft portion 409.

In some embodiments, the at least one first pitch and the at least one second pitch may not be equal to each other. In this manner, the distal helical thread portion with the second pitch may be advanced through a first bone portion and into a second bone portion (not shown). Then, as the proximal helical thread portion with the first pitch enters into the first bone portion, continued rotation of the fastener 400 will compress the two bone portions toward each other due to the difference in thread pitch between the proximal and distal helical thread portions. A predetermined amount of compression/displacement between the two bone portions may be achieved based on the lengths of the proximal and distal helical thread portions and/or the difference in pitch between the proximal and distal helical thread portions.

In some embodiments, the plurality of pitches may comprise one or more continuously variable pitches. For example, in some embodiments the fastener 400 may include a single helical thread disposed about the shaft 405 between the proximal and distal ends 401, 402 of the shaft 405 comprising a continuously variable pitch (not shown).

In some embodiments, the continuously variable pitch may decrease in a continuously variable manner moving from the distal end 402 of the shaft 405 toward the proximal end 401 of the shaft 405.

In some embodiments, the continuously variable pitch may increase in a continuously variable manner moving from the distal end 402 of the shaft 405 toward the proximal end 401 of the shaft 405.

In some embodiments, the plurality of pitches may include a first pitch 471 along the proximal shaft portion 408 and a second pitch 472 along the distal shaft portion 409, as shown in FIG. 4D.

Is some embodiments, the first pitch 471 and/or the second pitch 472 may be discrete.

In some embodiments, the first pitch 471 may be less than the second pitch 472.

In some embodiments, the first pitch 471 may be greater than the second pitch 472.

In some embodiments, the thickness of the first helical thread 410 may be increased or decreased in size and the first pitch 471 may remain constant irrespective of a selected thickness for the first helical thread 410.

In some embodiments, the thickness of the second helical thread 420 may be increased or decreased in size and the second pitch 472 may remain constant irrespective of a selected thickness for the second helical thread 420.

In some embodiments, the fastener 400 may comprise a "dual start" thread configuration at the distal shaft portion 409 (e.g., with greater pitch) and a "single start" thread configuration at the proximal shaft portion 408 (e.g., with smaller pitch). This configuration may achieve increased thread engagement with bone toward the distal end 402 of the fastener 400, while maintaining compression with the different thread pitches between the proximal and distal ends 401, 402 of the fastener 400.

In some embodiments, the fastener 400 may comprise a "dual start" thread configuration at the proximal shaft portion 408 (e.g., with greater pitch) and a "single start" thread configuration at the distal shaft portion 409 (e.g., with smaller pitch). This configuration to achieve increased thread engagement with bone toward the proximal end 401 of the fastener 400, while maintaining compression with the different thread pitches between the proximal and distal ends 401, 402 of the fastener 400.

In some embodiments, the first concave undercut surface 431 of the first helical thread 410 may include a first inflection point 491 at a first inflection point height 495, and a first convex undercut surface 441 of the first helical thread 410 may include a second inflection point 492 at a second inflection point height 496.

In some embodiments, the second concave undercut surface 432 of the second helical thread 420 may include a third inflection point 493 at a third inflection point height 497, and a second convex undercut surface 442 of the second helical thread 420 may include a fourth inflection point 494 at a fourth inflection point height 498.

In some embodiments, the first inflection point height 495 may be equal to the third inflection point height 497, and the second inflection point height 496 may be equal to the fourth inflection point height 498. This configuration may help simplify the manufacturing process of helical threads having different thread heights, as will be discussed below in more detail with respect to FIGS. 7A-7C. However, it will also be understood that any/all of the first inflection point height 495, the second inflection point height 496, the third inflection point height 497, and/or the fourth inflection point height 498 may be selectively manufactured according to any height irrespective of each another.

In some embodiments, a distal end 434 of the first helical thread 410 may be "clocked" or "timed" with a proximal end 433 of the second helical thread 420, as shown in FIG. 4C. This may be accomplished by selecting an appropriate distance between the proximal end 433 of the second helical thread 420 and the distal end 434 of the first helical thread 410 in view of the thread pitch of the second helical thread 420. In this manner, the distal end 434 of the first helical thread 410 may begin threading into a bone where the proximal end 433 of the second helical thread 420 left off to facilitate insertion of the fastener 400 into the bone and/or reduce cross-cutting of the bone to increase bone preservation.

In some embodiments, the one or more cutting flutes 407 may be shaped to urge bone chips (produced by the self-tapping action of the fastener 500) in at least one direction along the shaft 405 as the fastener 400 is rotated into a bone.

For example, the cutting flute 407 that is formed in the distal shaft portion 409 of the fastener 400 in FIG. 4C has a "left-handed" orientation 445, while the first and second helical threads 410, 420 are "right-handed". Thus, as the fastener 400 is inserted into a bone by rotating the fastener 400 clock-wise, the left-handed orientation 445 of this distal cutting flute 407 will tend to urge bone chips in the proximal-to-distal direction 444, as shown in FIG. 4C. This may help reduce friction/interference from bone chips and facilitate insertion of the fastener 400 into the bone.

Figure 6A:
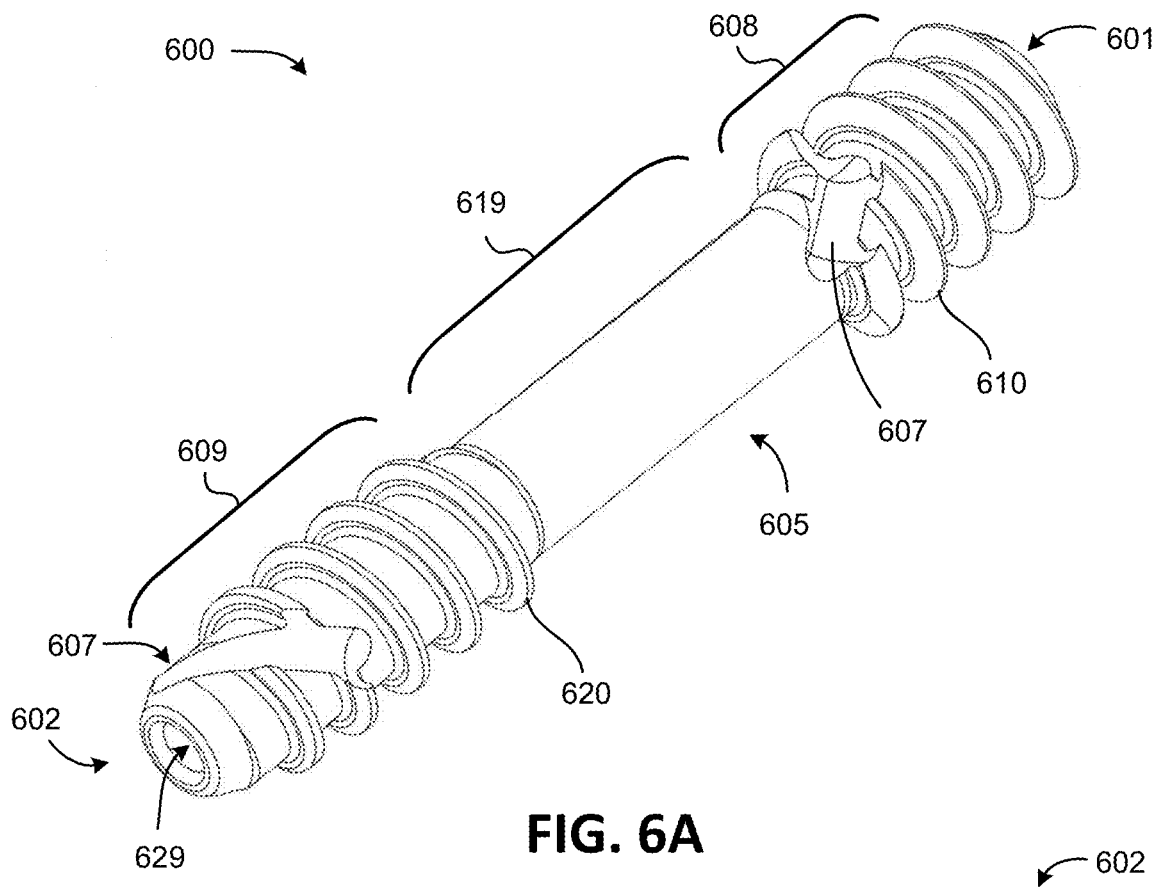
FIG. 6A illustrates a front perspective view of a fastener, according to an embodiment of the present disclosure.
Figure 6B:
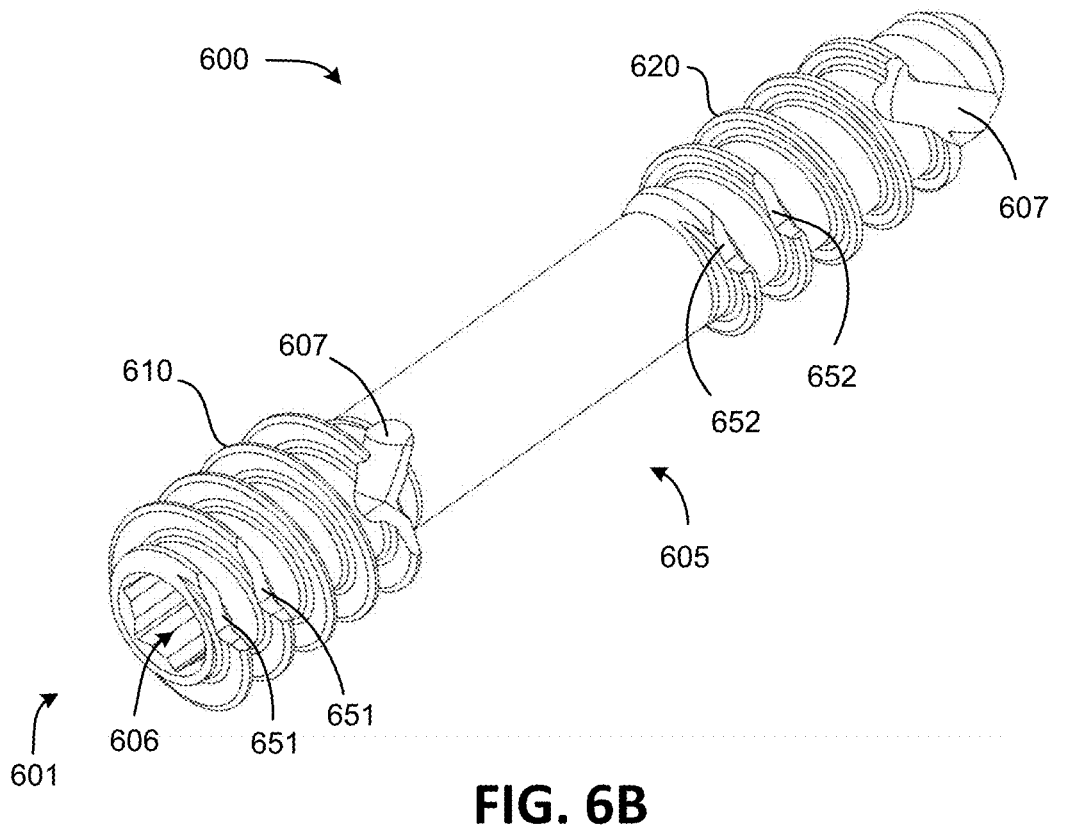
FIG. 6B illustrates a rear perspective view of the fastener of FIG. 6A.
Figure 6C:
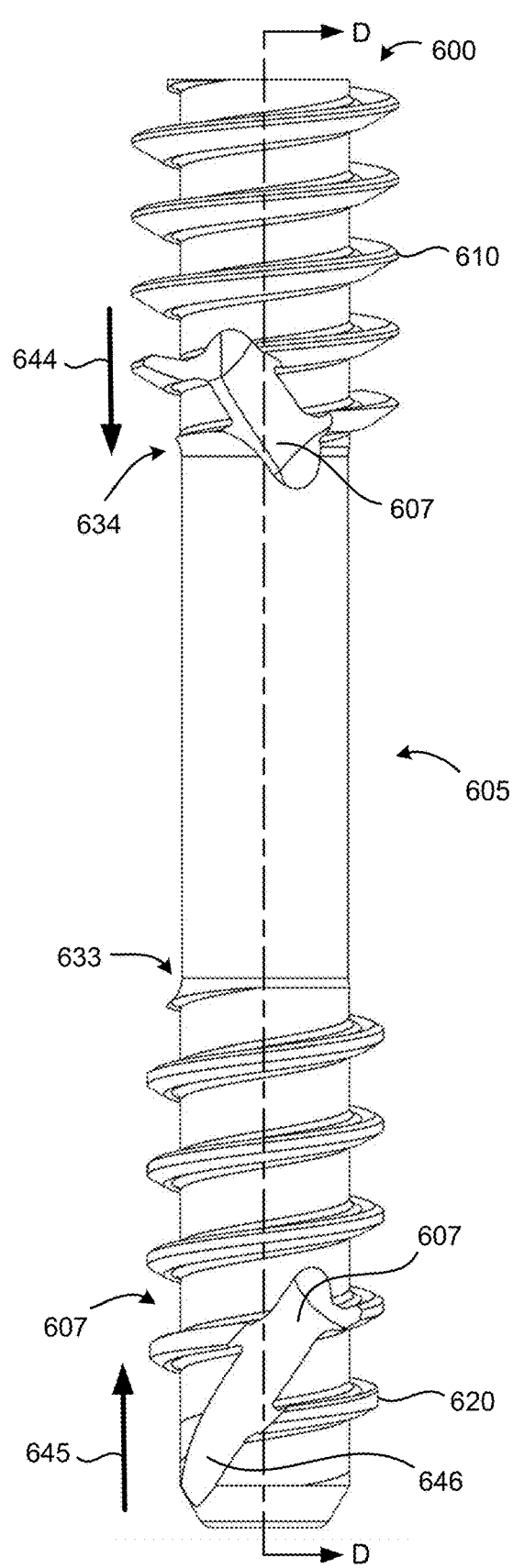
FIG. 6C illustrates a side view of the fastener of FIG. 6A.

Alternatively, the cutting flute 607 that is formed in the distal shaft portion 609 of the fastener 600 in FIG. 6C has a "right-handed" orientation 646. Thus, as the fastener 600 is inserted into a bone by rotating the fastener 600 clockwise, the right-handed orientation 646 of the distal cutting flute 607 will tend to urge bone chips in the distal-to-proximal direction 645, as shown in FIG. 6C. In this manner, bone chips may be directed back toward the intermediate shaft portion 619 (and/or toward a bone fracture in this region) to help facilitate bone growth/remodeling and the healing process. Moreover, in some embodiments the cutting flute 607 that is formed in the proximal shaft portion 608 of the fastener 600 in FIG. 6C may have a "left-handed" orientation. Thus, as the fastener 600 is inserted into a bone by rotating the fastener 600 clock-wise, the left-handed orientation of this proximal cutting flute 607 will tend to urge bone chips in the proximal-to-distal direction 644 shown in FIG. 6C. In this manner, these bone chips may be directed forward toward the intermediate shaft portion 619 (and/or toward a bone fracture in this region) to help facilitate bone growth/remodeling and the healing process.

In some embodiments, a first cutting flute 407 may be formed in the proximal shaft portion 408 and a second cutting flute 407 may be formed in the distal shaft portion 409.

In some embodiments, the first and second cutting flutes 407 may each be configured to urge bone chips in a proximal-to-distal direction along the shaft 405 as the fastener 400 is rotated into a bone.

In some embodiments, the first and second cutting flutes 407 may each be configured to urge bone chips in a distal-to-proximal direction along the shaft 405 as the fastener 400 is rotated into a bone.

In some embodiments, the first cutting flute 407 may be configured to urge bone chips in a proximal-to-distal direction along the shaft 405 as the fastener 400 is rotated into a bone, and the second cutting flute 407 may be configured to urge bone chips in a distal-to-proximal direction along the shaft 405 as the fastener 400 is rotated into the bone.

In some embodiments, the first cutting flute 407 may be configured to urge bone chips in a distal-to-proximal direction along the shaft 405 as the fastener 400 is rotated into a bone, and the second cutting flute 407 may be configured to urge bone chips in a proximal-to-distal direction along the shaft 405 as the fastener 400 is rotated into the bone.

In some embodiments, the proximal shaft portion 408 may include one or more proximal reverse cutting flutes 451 to facilitate removal of the fastener 400 from a bone after the healing process has occurred.

In some embodiments, the distal shaft portion 409 may include one or more distal reverse cutting flutes 452 to facilitate removal of the fastener 400 from a bone after the healing process has occurred.

Figure 5A:
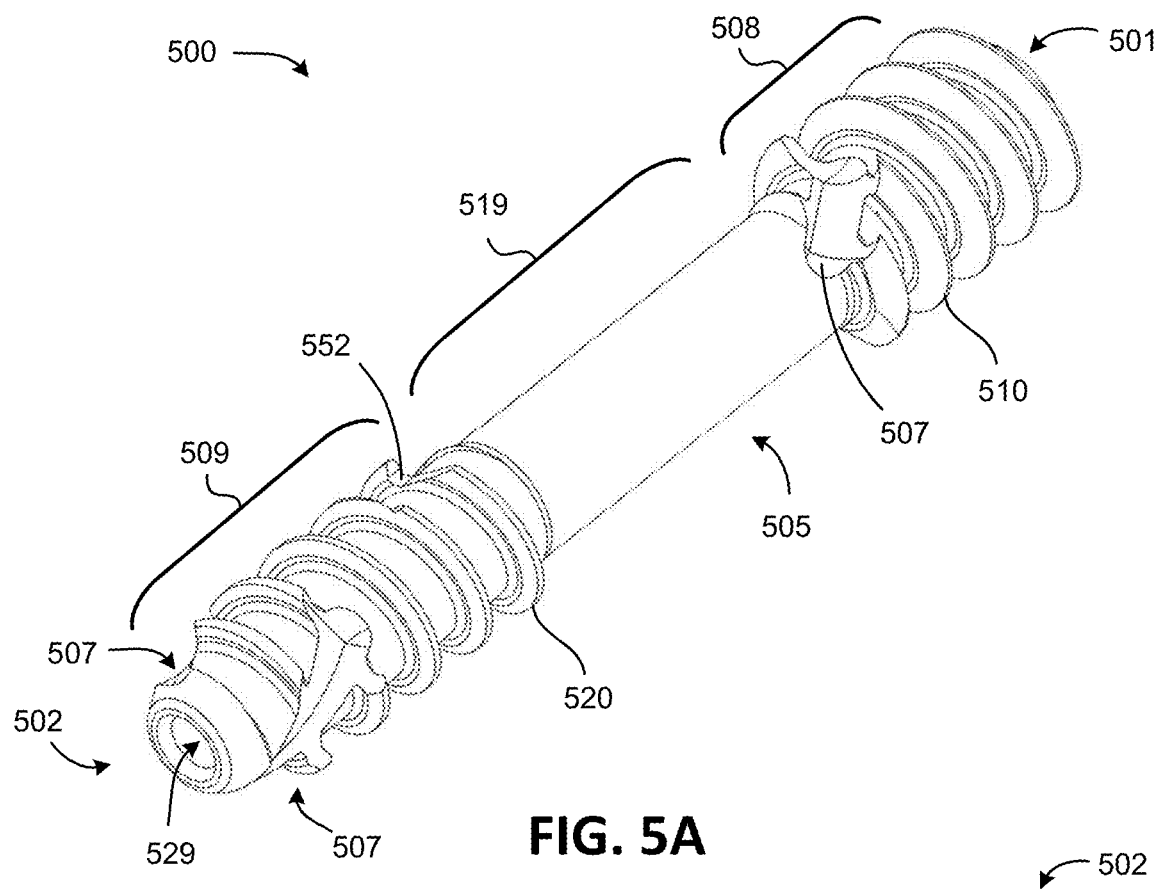
FIG. 5A illustrates a front perspective view of a fastener, according to an embodiment of the present disclosure.
Figure 5B:
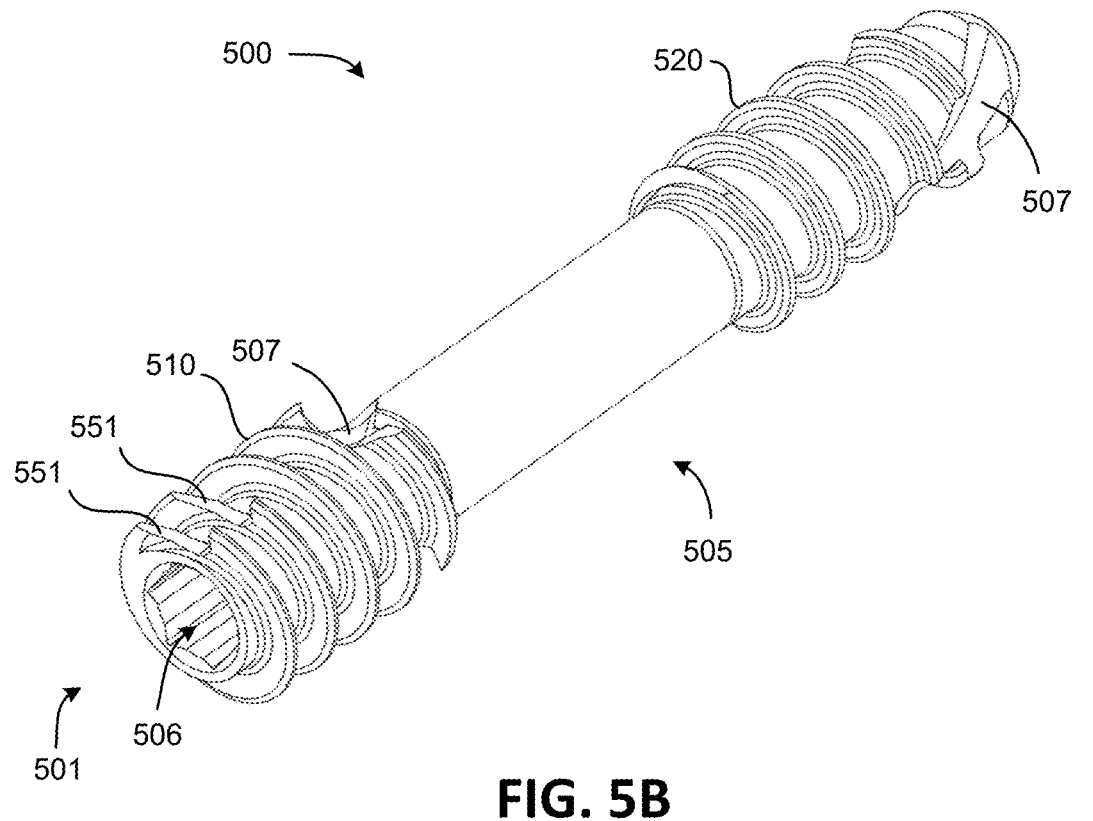
FIG. 5B illustrates a rear perspective view of the fastener of FIG. 5A.
Figure 5C:
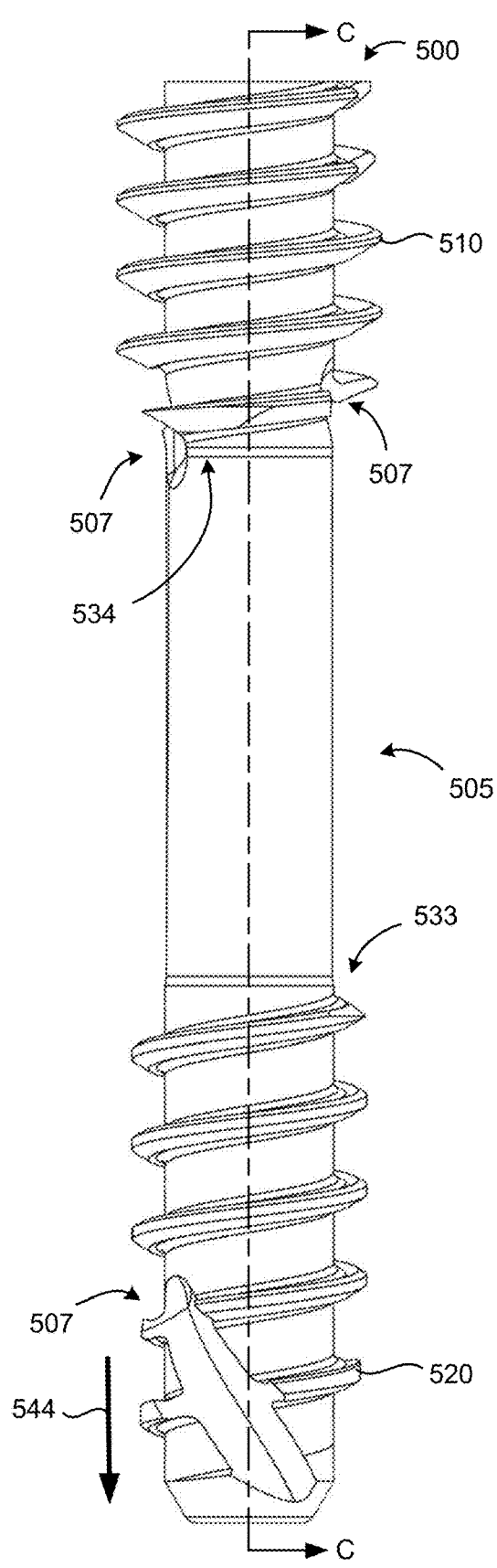
FIG. 5C illustrates a side view of the fastener of FIG. 5A.
Figure 5D:
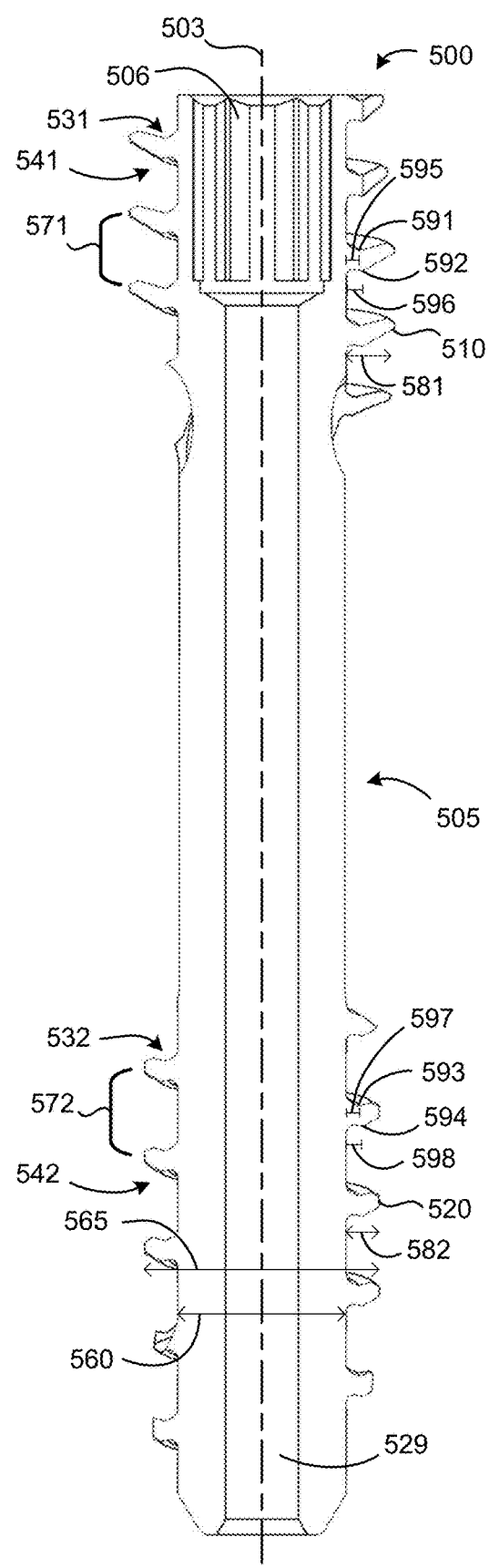
FIG. 5D illustrates a cross-sectional side view of the fastener of FIG. 5A taken along the line C-C shown in FIG. 5C.

FIGS. 5A-5D illustrate various views of a compression fastener, bone fastener, or fastener 500, according to another embodiment of the present disclosure. Specifically, FIG. 5A is a front perspective view of the fastener 500, FIG. 5B is a rear perspective view of the fastener 500, FIG. 5C is a side view of the fastener 500, and FIG. 5D is a cross-sectional side view of the fastener 500 taken along the line C-C in FIG. 5C.

The fastener 500 may generally include a shaft 505 having a proximal end 501, a distal end 502, a longitudinal axis 503, a proximal shaft portion 508, a distal shaft portion 509, an intermediate shaft portion 519, a first helical thread 510, a second helical thread 520, one or more cutting flutes 507 (and/or reverse cutting flutes), a central longitudinal passageway 529 to enable guided insertion of the fastener 500 over a K-wire or pin (not shown), and a torque connection interface 506.

In some embodiments, the fastener 500 may have a minor diameter 560 defined by the shaft 505 of the fastener 500.

In some embodiments, at least a portion of the minor diameter 560 may be constant along the shaft 505 of the fastener 500.

In some embodiments, at least a portion of the minor diameter 560 may vary along the shaft 505 of the fastener 500.

In some embodiments, the minor diameter of the distal shaft portion 509, the intermediate shaft portion 519, and/or the proximal shaft portion 508 may be constant and/or substantially equal to each other.

In some embodiments, at least a portion of the minor diameter 560 of the distal shaft portion 509 may be smaller than the minor diameter of the intermediate shaft portion 519 and/or the proximal shaft portion 508.

In some embodiments, the fastener 500 may have a major diameter 565 defined by one or more helical threads disposed about the shaft 505 of the fastener 500.

In some embodiments, the one or more helical threads may be disposed about the shaft 505 or portions of the shaft 505, as previously discussed.

In some embodiments, the fastener 500 may include a first helical thread 510 and a second helical thread 520 separated by a smooth shaft portion or intermediate shaft portion 519.

In some embodiments, the fastener 500 may include a single helical thread disposed about the shaft 505 between the proximal and distal ends 501, 502 of the shaft 505 (not shown). In these embodiments, the single helical thread may span the distal shaft portion 509, the intermediate shaft portion 519, and the proximal shaft portion 508. In these embodiments, the intermediate shaft portion 519 may not be threadless/smooth.

In some embodiments, the fastener 500 may include multiple helical threads disposed about the shaft 505 between the proximal and distal ends 501, 502 of the shaft 505 (not shown). In these embodiments, some or all of the helical threads may span the distal shaft portion 509, the intermediate shaft portion 519, and/or the proximal shaft portion 508. In these embodiments, the intermediate shaft portion 519 may not be threadless/smooth.

In some embodiments, at least a portion of the major diameter 565 may be constant along the one or more helical threads of the fastener 500.

In some embodiments, at least a portion of the major diameter 565 may vary along the one or more helical threads of the fastener 500.

In some embodiments, the major diameter 565 of the one or more helical threads about the distal shaft portion 509, the intermediate shaft portion 519, and/or the proximal shaft portion 508 may be constant and/or substantially equal to each other.

In some embodiments, the major diameter 565 of the one or more helical threads about the distal shaft portion 509, the intermediate shaft portion 519, and/or the proximal shaft portion 508 may not be constant and/or not substantially equal to each other.

In some embodiments, the major diameter 565 of the one or more helical threads about the distal shaft portion 509, the intermediate shaft portion 519, and/or the proximal shaft portion 508 may be continuously variable.

In some embodiments, the major diameter 565 of the one or more helical threads may increase in a continuously variable manner from the distal end 502 of the shaft 505 toward the proximal end 501 of the shaft 505.

In some embodiments, the major diameter 565 of the one or more helical threads may decrease in a continuously variable manner from the distal end 502 of the shaft 505 toward the proximal end 501 of the shaft 505.

In some embodiments, the major diameter 565 of the one or more helical threads may decrease in a continuously variable manner from the distal end 502 of the shaft 505 toward the intermediate shaft portion 519, then increase in a continuously variable manner from the intermediate shaft portion 519 toward the proximal end 501 of the shaft 505.

In some embodiments, the major diameter 565 of the one or more helical threads may increase in a continuously variable manner from the distal end 502 of the shaft 505 toward the intermediate shaft portion 519, then decrease in a continuously variable manner from the intermediate shaft portion 519 toward the proximal end 501 of the shaft 505.

In some embodiments, the major diameter 565 or first height 581 of the first helical thread 510 disposed about the proximal shaft portion 508 may be equal to the major diameter 565 or second height 582 of the second helical thread 520 disposed about the distal shaft portion 509.

In some embodiments, the major diameter 565 or first height 581 of the first helical thread 510 disposed about the proximal shaft portion 508 may not be equal to the major diameter 565 or second height 582 of the second helical thread 520 disposed about the distal shaft portion 509.

In some embodiments, the major diameter 565 or first height 581 of the first helical thread 510 disposed about the proximal shaft portion 508 may be greater than the major diameter 565 or second height 582 of the second helical thread 520 disposed about the distal shaft portion 509. This may allow for greater bone purchase by the first helical thread 510.

However, it will also be understood that in some embodiments the major diameter 565 or first height 581 of the first helical thread 510 disposed about the proximal shaft portion 508 may be less than the major diameter 565 or second height 582 of the second helical thread 520 disposed about the distal shaft portion 509. This may allow for greater bone purchase by the second helical thread 520.

In some embodiments, the one or more helical threads disposed about the shaft 505 may include at least one concave undercut surface. The at least one concave undercut surface may be angled towards one of the proximal end 501 and the distal end 502 of the shaft 505.

In some embodiments, the first helical thread 510 may include a first concave undercut surface 531, and the second helical thread 520 may include a second concave undercut surface 532. The first and second concave undercut surfaces 531, 532 may be angled towards one of the proximal end 501 and the distal end 502 of the shaft 505.

However, it will also be understood that the fastener 500 may include any thread configuration, feature, size, morphology, etc., that is described or contemplated herein to achieve optimal fixation within a given bone/tissue. For example, in some embodiments the one or more helical threads may comprise standard or inverted threading (or combinations thereof), a "dual start" thread configuration, crescent shapes, chevron shapes, etc.

In some embodiments, the one or more helical threads may include a plurality of pitches.

In some embodiments, the plurality of pitches may include at least one first pitch along the proximal shaft portion 508, and at least one second pitch along the distal shaft portion 509.

In some embodiments, the at least one first pitch and the at least one second pitch may not be equal to each other. In this manner, the distal helical thread portion with the second pitch may be advanced through a first bone portion and into a second bone portion (not shown). Then, as the proximal helical thread portion with the first pitch enters into the first bone portion, continued rotation of the fastener 500 will compress the two bone portions toward each other due to the difference in thread pitch between the proximal and distal helical thread portions. A predetermined amount of compression/displacement between the two bone portions may be achieved based on the lengths of the proximal and distal helical thread portions and/or the difference in pitch between the proximal and distal helical thread portions.

In some embodiments, the plurality of pitches may comprise one or more continuously variable pitches. For example, in some embodiments the fastener 500 may include a single helical thread disposed about the shaft 505 between the proximal and distal ends 501, 502 of the shaft 505 comprising a continuously variable pitch (not shown).

In some embodiments, the continuously variable pitch may decrease in a continuously variable manner moving from the distal end 502 of the shaft 505 toward the proximal end 501 of the shaft 505.

In some embodiments, the continuously variable pitch may increase in a continuously variable manner moving from the distal end 502 of the shaft 505 toward the proximal end 501 of the shaft 505.

In some embodiments, the plurality of pitches may include a first pitch 571 along the proximal shaft portion 508 and a second pitch 572 along the distal shaft portion 509, as shown in FIG. 5D.

Is some embodiments, the first pitch 571 and/or the second pitch 572 may be discrete.

In some embodiments, the first pitch 571 may be less than the second pitch 572.

In some embodiments, the first pitch 571 may be greater than the second pitch 572.

In some embodiments, the thickness of the first helical thread 510 may be increased or decreased in size and the first pitch 571 may remain constant irrespective of a selected thickness for the first helical thread 510.

In some embodiments, the thickness of the second helical thread 520 may be increased or decreased in size and the second pitch 572 may remain constant irrespective of a selected thickness for the second helical thread 520.

In some embodiments, the fastener 500 may comprise a "dual start" thread configuration at the distal shaft portion 509 (e.g., with greater pitch) and a "single start" thread configuration at the proximal shaft portion 508 (e.g., with smaller pitch). This configuration may achieve increased thread engagement with bone toward the distal end 502 of the fastener 500, while maintaining compression with the different thread pitches between the proximal and distal ends 501, 502 of the fastener 500.

In some embodiments, the fastener 500 may comprise a "dual start" thread configuration at the proximal shaft portion 508 (e.g., with greater pitch) and a "single start" thread configuration at the distal shaft portion 509 (e.g., with smaller pitch). This configuration to achieve increased thread engagement with bone toward the proximal end 501 of the fastener 500, while maintaining compression with the different thread pitches between the proximal and distal ends 501, 502 of the fastener 500.

In some embodiments, the first concave undercut surface 531 of the first helical thread 510 may include a first inflection point 591 at a first inflection point height 595, and a first convex undercut surface 541 of the first helical thread 510 may include a second inflection point 592 at a second inflection point height 596.

In some embodiments, the second concave undercut surface 532 of the second helical thread 520 may include a third inflection point 593 at a third inflection point height 597, and a second convex undercut surface 542 of the second helical thread 520 may include a fourth inflection point 594 at a fourth inflection point height 598.

In some embodiments, the first inflection point height 595 may be equal to the third inflection point height 597, and the second inflection point height 596 may be equal to the fourth inflection point height 598. This configuration may help simplify the manufacturing process of helical threads having different thread heights, as will be discussed below in more detail with respect to FIGS. 7A-7C. However, it will also be understood that any/all of the first inflection point height 595, the second inflection point height 596, the third inflection point height 597, and/or the fourth inflection point height 598 may be selectively manufactured according to any height irrespective of each another.

In some embodiments, a distal end 534 of the first helical thread 510 may be "clocked" or "timed" with a proximal end 533 of the second helical thread 520, as shown in FIG. 5C. This may be accomplished by selecting an appropriate distance between the proximal end 533 of the second helical thread 520 and the distal end 534 of the first helical thread 510 in view of the thread pitch of the second helical thread 520. In this manner, the distal end 534 of the first helical thread 510 may begin threading into a bone where the proximal end 533 of the second helical thread 520 left off to facilitate insertion of the fastener 500 into the bone and/or reduce cross-cutting of the bone to increase bone preservation.

As previously discussed, the one or more cutting flutes 507 may be shaped to urge bone chips (produced by the self-tapping action of the fastener 500) in at least one direction along the shaft 505 as the fastener 500 is rotated into a bone.

In some embodiments, a first cutting flute 507 may be formed in the proximal shaft portion 508 and a second cutting flute 507 may be formed in the distal shaft portion 509.

In some embodiments, the first and second cutting flutes 507 may each be configured to urge bone chips in a proximal-to-distal direction 544 along the shaft 505 as the fastener 500 is rotated into a bone.

In some embodiments, the first and second cutting flutes 507 may each be configured to urge bone chips in a distal-to-proximal direction along the shaft 505 as the fastener 500 is rotated into a bone.

In some embodiments, the first cutting flute 507 may be configured to urge bone chips in a proximal-to-distal direction along the shaft 505 as the fastener 500 is rotated into a bone, and the second cutting flute 507 may be configured to urge bone chips in a distal-to-proximal direction along the shaft 505 as the fastener 500 is rotated into the bone.

In some embodiments, the first cutting flute 507 may be configured to urge bone chips in a distal-to-proximal direction along the shaft 505 as the fastener 500 is rotated into a bone, and the second cutting flute 507 may be configured to urge bone chips in a proximal-to-distal direction along the shaft 505 as the fastener 500 is rotated into the bone.

In some embodiments, the proximal shaft portion 508 may include one or more proximal reverse cutting flutes 551 to facilitate removal of the fastener 500 from a bone after the healing process has occurred.

In some embodiments, the distal shaft portion 509 may include one or more distal reverse cutting flutes 552 to facilitate removal of the fastener 500 from a bone after the healing process has occurred.

Figure 6D:
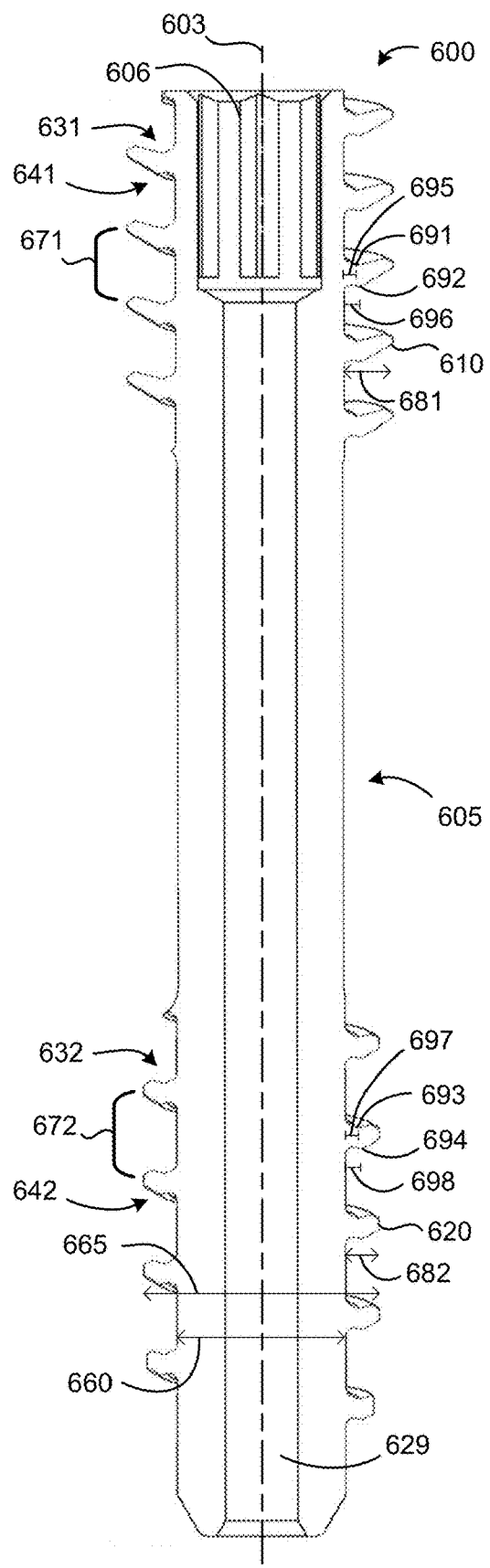
FIG. 6D illustrates a cross-sectional side view of the fastener of FIG. 6A taken along the line B-B shown in FIG. 6C.

FIGS. 6A-6D illustrate various views of a compression fastener, bone fastener, or fastener 600, according to another embodiment of the present disclosure. Specifically, FIG. 6A is a front perspective view of the fastener 600, FIG. 6B is a rear perspective view of the fastener 600, FIG. 6C is a side view of the fastener 600, and FIG. 6D is a cross-sectional side view of the fastener 600 taken along the line D-D in FIG. 6C.

The fastener 600 may generally include a shaft 605 having a proximal end 601, a distal end 602, a longitudinal axis 603, a proximal shaft portion 608, a distal shaft portion 609, an intermediate shaft portion 619, a first helical thread 610, a second helical thread 620, one or more cutting flutes 607 (and/or reverse cutting flutes), a central longitudinal passageway 629 to enable guided insertion of the fastener 600 over a K-wire or pin (not shown), and a torque connection interface 606.

In some embodiments, the fastener 600 may have a minor diameter 660 defined by the shaft 605 of the fastener 600.

In some embodiments, at least a portion of the minor diameter 660 may be constant along the shaft 605 of the fastener 600.

In some embodiments, at least a portion of the minor diameter 660 may vary along the shaft 605 of the fastener 600.

In some embodiments, the minor diameter of the distal shaft portion 609, the intermediate shaft portion 619, and/or the proximal shaft portion 608 may be constant and/or substantially equal to each other.

In some embodiments, at least a portion of the minor diameter 660 of the distal shaft portion 609 may be smaller than the minor diameter of the intermediate shaft portion 619 and/or the proximal shaft portion 608.

In some embodiments, the fastener 600 may have a major diameter 665 defined by one or more helical threads disposed about the shaft 605 of the fastener 600.

In some embodiments, the one or more helical threads may be disposed about the shaft 605 or portions of the shaft 605, as previously discussed.

In some embodiments, the fastener 600 may include a first helical thread 610 and a second helical thread 620 separated by a smooth shaft portion or intermediate shaft portion 619.

In some embodiments, the fastener 600 may include a single helical thread disposed about the shaft 605 between the proximal and distal ends 601, 602 of the shaft 605 (not shown). In these embodiments, the single helical thread may span the distal shaft portion 609, the intermediate shaft portion 619, and the proximal shaft portion 608. In these embodiments, the intermediate shaft portion 619 may not be threadless/smooth.

In some embodiments, the fastener 600 may include multiple helical threads disposed about the shaft 605 between the proximal and distal ends 601, 602 of the shaft 605 (not shown). In these embodiments, some or all of the helical threads may span the distal shaft portion 609, the intermediate shaft portion 619, and/or the proximal shaft portion 608. In these embodiments, the intermediate shaft portion 619 may not be threadless/smooth.

In some embodiments, at least a portion of the major diameter 665 may be constant along the one or more helical threads of the fastener 600.

In some embodiments, at least a portion of the major diameter 665 may vary along the one or more helical threads of the fastener 600.

In some embodiments, the major diameter 665 of the one or more helical threads about the distal shaft portion 609, the intermediate shaft portion 619, and/or the proximal shaft portion 608 may be constant and/or substantially equal to each other.

In some embodiments, the major diameter 665 of the one or more helical threads about the distal shaft portion 609, the intermediate shaft portion 619, and/or the proximal shaft portion 608 may not be constant and/or not substantially equal to each other.

In some embodiments, the major diameter 665 of the one or more helical threads about the distal shaft portion 609, the intermediate shaft portion 619, and/or the proximal shaft portion 608 may be continuously variable.

In some embodiments, the major diameter 665 of the one or more helical threads may increase in a continuously variable manner from the distal end 602 of the shaft 605 toward the proximal end 601 of the shaft 605.

In some embodiments, the major diameter 665 of the one or more helical threads may decrease in a continuously variable manner from the distal end 602 of the shaft 605 toward the proximal end 601 of the shaft 605.

In some embodiments, the major diameter 665 of the one or more helical threads may decrease in a continuously variable manner from the distal end 602 of the shaft 605 toward the intermediate shaft portion 619, then increase in a continuously variable manner from the intermediate shaft portion 619 toward the proximal end 601 of the shaft 605.

In some embodiments, the major diameter 665 of the one or more helical threads may increase in a continuously variable manner from the distal end 602 of the shaft 605 toward the intermediate shaft portion 619, then decrease in a continuously variable manner from the intermediate shaft portion 619 toward the proximal end 601 of the shaft 605.

In some embodiments, the major diameter 665 or first height 681 of the first helical thread 610 disposed about the proximal shaft portion 608 may be equal to the major diameter 665 or second height 682 of the second helical thread 620 disposed about the distal shaft portion 609.

In some embodiments, the major diameter 665 or first height 681 of the first helical thread 610 disposed about the proximal shaft portion 608 may not be equal to the major diameter 665 or second height 682 of the second helical thread 620 disposed about the distal shaft portion 609.

In some embodiments, the major diameter 665 or first height 681 of the first helical thread 610 disposed about the proximal shaft portion 608 may be greater than the major diameter 665 or second height 682 of the second helical thread 620 disposed about the distal shaft portion 609. This may allow for greater bone purchase by the first helical thread 610.

However, it will also be understood that in some embodiments the major diameter 665 or first height 681 of the first helical thread 610 disposed about the proximal shaft portion 608 may be less than the major diameter 665 or second height 682 of the second helical thread 620 disposed about the distal shaft portion 609. This may allow for greater bone purchase by the second helical thread 620.

In some embodiments, the one or more helical threads disposed about the shaft 605 may include at least one concave undercut surface. The at least one concave undercut surface may be angled towards one of the proximal end 601 and the distal end 602 of the shaft 605.

In some embodiments, the first helical thread 610 may include a first concave undercut surface 631, and the second helical thread 620 may include a second concave undercut surface 632. The first and second concave undercut surfaces 631, 632 may be angled towards one of the proximal end 601 and the distal end 602 of the shaft 605.

However, it will also be understood that the fastener 600 may include any thread configuration, feature, size, morphology, etc., that is described or contemplated herein to achieve optimal fixation within a given bone/tissue. For example, in some embodiments the one or more helical threads may comprise standard or inverted threading (or combinations thereof), a "dual start" thread configuration, crescent shapes, chevron shapes, etc.

In some embodiments, the one or more helical threads may include a plurality of pitches.

In some embodiments, the plurality of pitches may include at least one first pitch along the proximal shaft portion 608, and at least one second pitch along the distal shaft portion 609.

In some embodiments, the at least one first pitch and the at least one second pitch may not be equal to each other. In this manner, the distal helical thread portion with the second pitch may be advanced through a first bone portion and into a second bone portion (not shown). Then, as the proximal helical thread portion with the first pitch enters into the first bone portion, continued rotation of the fastener 600 will compress the two bone portions toward each other due to the difference in thread pitch between the proximal and distal helical thread portions. A predetermined amount of compression/displacement between the two bone portions may be achieved based on the lengths of the proximal and distal helical thread portions and/or the difference in pitch between the proximal and distal helical thread portions.

In some embodiments, the plurality of pitches may comprise one or more continuously variable pitches. For example, in some embodiments the fastener 600 may include a single helical thread disposed about the shaft 605 between the proximal and distal ends 601, 602 of the shaft 605 comprising a continuously variable pitch (not shown).

In some embodiments, the continuously variable pitch may decrease in a continuously variable manner moving from the distal end 602 of the shaft 605 toward the proximal end 601 of the shaft 605.

In some embodiments, the continuously variable pitch may increase in a continuously variable manner moving from the distal end 602 of the shaft 605 toward the proximal end 601 of the shaft 605.

In some embodiments, the plurality of pitches may include a first pitch 671 along the proximal shaft portion 608 and a second pitch 672 along the distal shaft portion 609, as shown in FIG. 6D.

Is some embodiments, the first pitch 671 and/or the second pitch 672 may be discrete.

In some embodiments, the first pitch 671 may be less than the second pitch 672.

In some embodiments, the first pitch 671 may be greater than the second pitch 672.

In some embodiments, the thickness of the first helical thread 610 may be increased or decreased in size and the first pitch 671 may remain constant irrespective of a selected thickness for the first helical thread 610.

In some embodiments, the thickness of the second helical thread 620 may be increased or decreased in size and the second pitch 672 may remain constant irrespective of a selected thickness for the second helical thread 620.

In some embodiments, the fastener 600 may comprise a "dual start" thread configuration at the distal shaft portion 609 (e.g., with greater pitch) and a "single start" thread configuration at the proximal shaft portion 608 (e.g., with smaller pitch). This configuration may achieve increased thread engagement with bone toward the distal end 602 of the fastener 600, while maintaining compression with the different thread pitches between the proximal and distal ends 601, 602 of the fastener 600.

In some embodiments, the fastener 600 may comprise a "dual start" thread configuration at the proximal shaft portion 608 (e.g., with greater pitch) and a "single start" thread configuration at the distal shaft portion 609 (e.g., with smaller pitch). This configuration to achieve increased thread engagement with bone toward the proximal end 601 of the fastener 600, while maintaining compression with the different thread pitches between the proximal and distal ends 601, 602 of the fastener 600.

In some embodiments, the first concave undercut surface 631 of the first helical thread 610 may include a first inflection point 691 at a first inflection point height 695, and a first convex undercut surface 641 of the first helical thread 610 may include a second inflection point 692 at a second inflection point height 696.

In some embodiments, the second concave undercut surface 632 of the second helical thread 620 may include a third inflection point 693 at a third inflection point height 697, and a second convex undercut surface 642 of the second helical thread 620 may include a fourth inflection point 694 at a fourth inflection point height 698.

In some embodiments, the first inflection point height 695 may be equal to the third inflection point height 697, and the second inflection point height 696 may be equal to the fourth inflection point height 698. This configuration may help simplify the manufacturing process of helical threads having different thread heights, as will be discussed below in more detail with respect to FIGS. 7A-7C. However, it will also be understood that any/all of the first inflection point height 695, the second inflection point height 696, the third inflection point height 697, and/or the fourth inflection point height 698 may be selectively manufactured according to any height irrespective of each another.

In some embodiments, a distal end 634 of the first helical thread 610 may be "clocked" or "timed" with a proximal end 633 of the second helical thread 620, as shown in FIG. 6C. This may be accomplished by selecting an appropriate distance between the proximal end 633 of the second helical thread 620 and the distal end 634 of the first helical thread 610 in view of the thread pitch of the second helical thread 620. In this manner, the distal end 634 of the first helical thread 610 may begin threading into a bone where the proximal end 633 of the second helical thread 620 left off to facilitate insertion of the fastener 600 into the bone and/or reduce cross-cutting of the bone to increase bone preservation.

As previously discussed, the one or more cutting flutes 607 may be shaped to urge bone chips (produced by the self-tapping action of the fastener 600) in at least one direction along the shaft 605 as the fastener 600 is rotated into a bone.

In some embodiments, a first cutting flute 607 may be formed in the proximal shaft portion 608 and a second cutting flute 607 may be formed in the distal shaft portion 609.

In some embodiments, the first and second cutting flutes 607 may each be configured to urge bone chips in a proximal-to-distal direction along the shaft 605 as the fastener 600 is rotated into a bone.

In some embodiments, the first and second cutting flutes 607 may each be configured to urge bone chips in a distal-to-proximal direction along the shaft 605 as the fastener 600 is rotated into a bone.

In some embodiments, the first cutting flute 607 may be configured to urge bone chips in a proximal-to-distal direction along the shaft 605 as the fastener 600 is rotated into a bone, and the second cutting flute 607 may be configured to urge bone chips in a distal-to-proximal direction along the shaft 605 as the fastener 600 is rotated into the bone.

In some embodiments, the first cutting flute 607 may be configured to urge bone chips in a distal-to-proximal direction along the shaft 605 as the fastener 600 is rotated into a bone, and the second cutting flute 607 may be configured to urge bone chips in a proximal-to-distal direction along the shaft 605 as the fastener 600 is rotated into the bone.

In some embodiments, the proximal shaft portion 608 may include one or more proximal reverse cutting flutes 651 to facilitate removal of the fastener 600 from a bone after the healing process has occurred.

In some embodiments, the distal shaft portion 609 may include one or more distal reverse cutting flutes 652 to facilitate removal of the fastener 600 from a bone after the healing process has occurred.

Figure 7A:
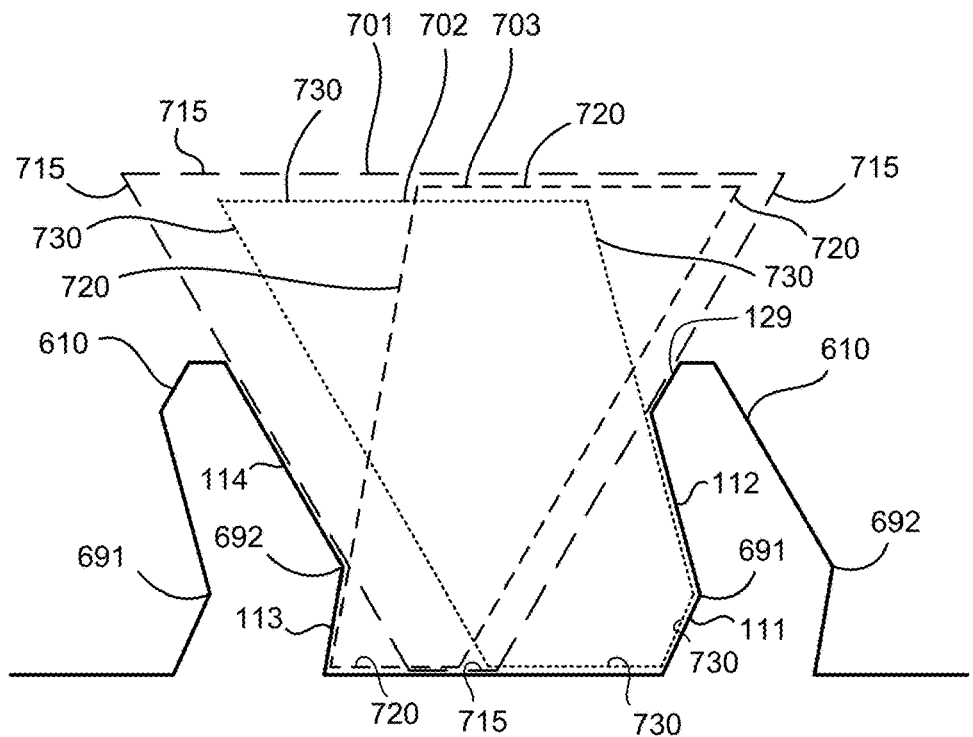
FIG. 7A illustrates a cutting process for forming a helical thread having a first height.
Figure 7B:
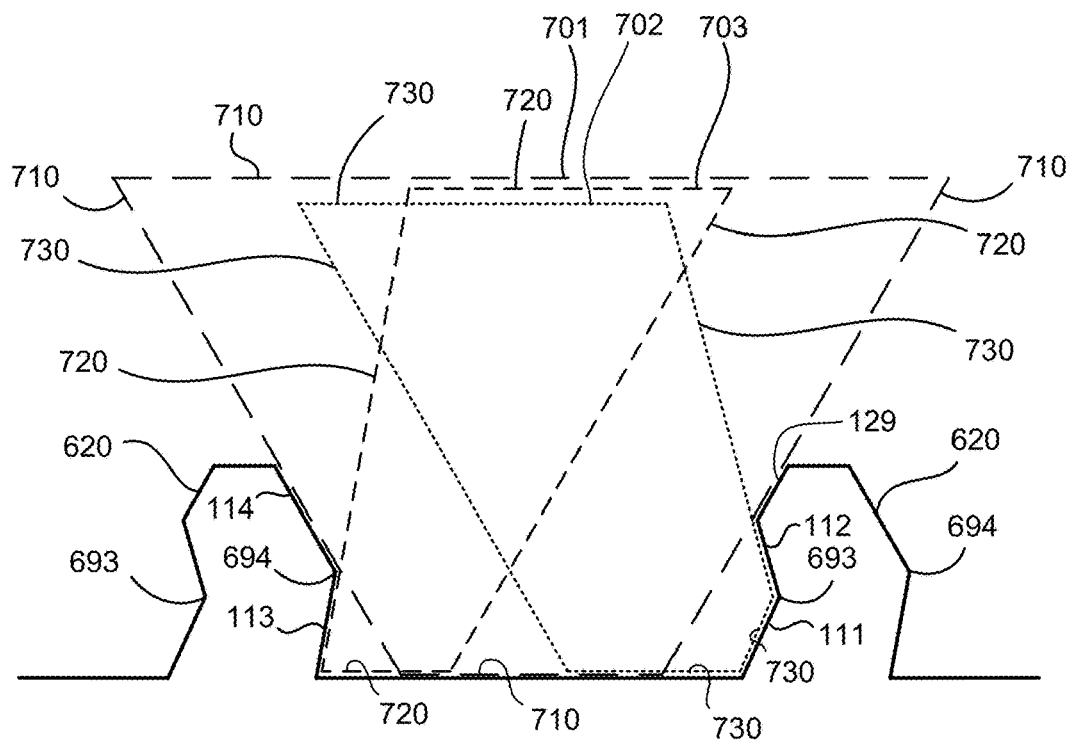
FIG. 7B illustrates a cutting process for forming a helical thread having a second height.
Figure 7C:
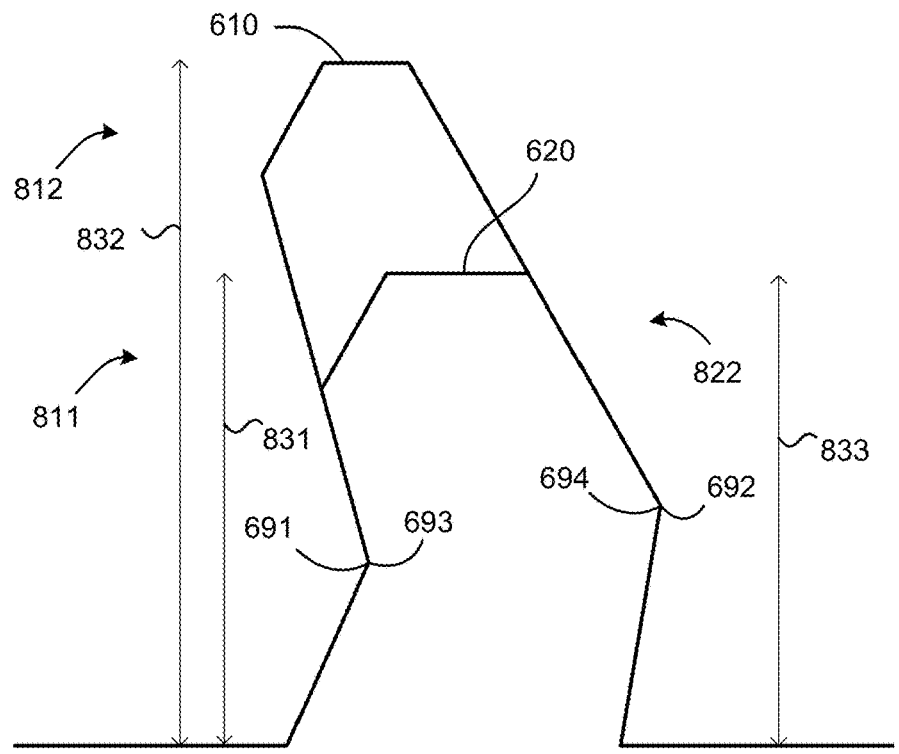
FIG. 7C illustrates the helical threads of FIGS. 7A and 7B overlaid on top of each other.
Figure 7D:
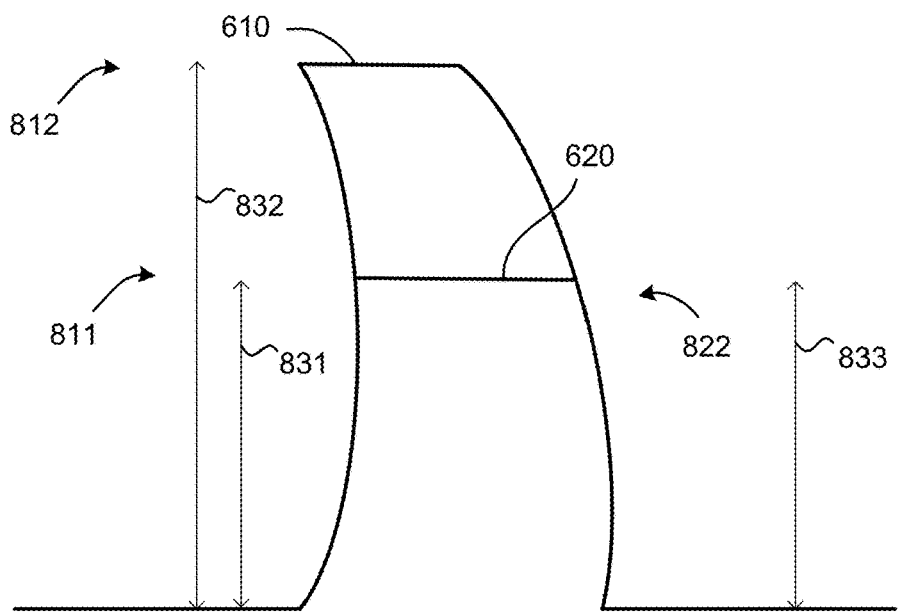
FIG. 7D illustrates the helical threads of FIGS. 7A and 7B overlaid on top of each other and utilizing the crescent shapes shown in FIG. 2.

FIGS. 7A and 7B illustrate a simplified cutting process for two helical threads on different portions of a shaft having different heights and pitches. FIG. 7C illustrates the helical threads shown in FIGS. 7A and 7B overlaid on top of each other, and FIG. 7D illustrates the helical threads of FIGS. 7A and 7B overlaid on top of each other, but utilizing the crescent shapes shown in FIG. 2. FIGS. 7A-7D will be discussed in terms of the helical threads shown in FIG. 6D, as one non-limiting example, for illustration purposes only. It will be understood that these cutting processes can apply to any other helical thread designs that are disclosed or contemplated herein.

FIG. 7A shows a cutting process for the first helical thread 610 having a first height 681 and a first pitch 671 (e.g., see FIG. 6D), and FIG. 7B shows a cutting process for the second helical thread 620 having a second height 682 and a second pitch 672. In this embodiment, the first height 681 may be greater than the second height 682, and the second pitch 672 may be greater than the first pitch 671.

FIG. 6D also shows the first inflection point 691 at the first inflection point height 695, the second inflection point 692 at the second inflection point height 696, the third inflection point 693 at the third inflection point height 697, and the fourth inflection point 694 at the fourth inflection point height 698.

In some embodiments, the first inflection point height 695 may be equal to the third inflection point height 697, and the second inflection point height 696 may be equal to the fourth inflection point height 698. This configuration may help simplify the manufacturing process of the first helical thread 610 and the second helical thread 620 by reducing the need to change out cutting tools during the manufacturing process.

For example, in a first step of the manufacturing process a first cutting tool 701 may be utilized to make a first cut in the shaft 605 of the fastener 600 to begin formation of the first helical thread 610, as shown in FIG. 7A. In some embodiments, the shape outlined by the four lines 715 shown in FIG. 7A may generally correspond to the shape of the first cutting tool 701 during this first step of the cutting process. In this step, the first cutting tool 701 may be placed at a proximal shaft portion of a substantially cylindrical substrate having a proximal end and a distal end (not shown), the substantially cylindrical substrate may be rotated about its longitudinal axis, and the first cutting tool 701 may be translated along the proximal shaft portion to form a fourth open surface 114 of the first helical thread 610, with the first helical thread 610 having a first pitch 671 and a first height 681.

In some embodiments, the manufacturing process may proceed to a second step in which the first cutting tool 701 may be utilized to make a second cut in the shaft 605 of the fastener 600 to begin formation of the second helical thread 620, as shown in FIG. 7B. In some embodiments, the shape outlined by the four lines 710 shown in FIG. 7A may generally correspond to the shape of the first cutting tool 701 during this second step of the cutting process (e.g., translating the first cutting tool 701 shown in FIG. 7A along the shaft 605 will form the wider cut for this portion of the second helical thread 620, as shown in FIG. 7B). In this step, the first cutting tool 701 may be placed at a distal shaft portion of the substantially cylindrical substrate, the substantially cylindrical substrate may be rotated about its longitudinal axis, and the first cutting tool 701 may be translated along the distal shaft portion to form a fourth open surface 114 of the second helical thread 620, with the second helical thread 620 having a second pitch 672 and a second height 682.

In some embodiments, the manufacturing process may proceed to a third step in which the second cutting tool 702 may be utilized to make a third cut in the shaft 605 of the fastener 600 to continue forming the first helical thread 610, as shown in FIG. 7A (e.g., forming the first concave undercut surface 631 shown in FIG. 6D). In some embodiments, the shape outlined by the five lines 730 shown in FIG. 7A may generally correspond to the shape of the second cutting tool 702 during this third step of the cutting process. In this step, the second cutting tool 702 may be placed at the proximal shaft portion of the substantially cylindrical substrate, the substantially cylindrical substrate may be rotated about its longitudinal axis, and the second cutting tool 702 may be translated along the proximal shaft portion to form a first undercut surface 111 and a second undercut surface 112 of the first helical thread 610.

In some embodiments, the manufacturing process may proceed to a fourth step in which the second cutting tool 702 may be utilized to make a fourth cut in the shaft 605 of the fastener 600 to continue forming the second helical thread 620, as shown in FIG. 7B (e.g., forming the second concave undercut surface 632 shown in FIG. 6D). In this step, the second cutting tool 702 may be placed at the distal shaft portion of the substantially cylindrical substrate, the substantially cylindrical substrate may be rotated about its longitudinal axis, and the second cutting tool 702 may be translated along the distal shaft portion to form a first undercut surface 111 and a second undercut surface 112 of the second helical thread 620.

In some embodiments, the manufacturing process may proceed to a fifth step in which the third cutting tool 703 may be utilized to make a fifth cut in the shaft 605 of the fastener 600 to continue forming the first helical thread 610, as shown in FIG. 7A (e.g., forming the first convex undercut surface 641 shown in FIG. 6D). In some embodiments, the shape outlined by the five lines 720 shown in FIG. 7A may generally correspond to the shape of the third cutting tool 703 during this third step of the cutting process. In this step, the third cutting tool 703 may be placed at the proximal shaft portion of the substantially cylindrical substrate, the substantially cylindrical substrate may be rotated about its longitudinal axis, and the third cutting tool 703 may be translated along the proximal shaft portion to form a third undercut surface 113 of the first helical thread 610.

In some embodiments, the manufacturing process may proceed to a sixth step in which the third cutting tool 703 may be utilized to make a sixth cut in the shaft 605 of the fastener 600 to continue forming the second helical thread 620, as shown in FIG. 7B (e.g., forming the second convex undercut surface 642 shown in FIG. 6D). In this step, the third cutting tool 703 may be placed at the distal shaft portion of the substantially cylindrical substrate, the substantially cylindrical substrate may be rotated about its longitudinal axis, and the third cutting tool 703 may be translated along the distal shaft portion to form a third undercut surface 113 of the second helical thread 620, and the manufacturing process may end.

In some embodiments, the manufacturing process may also include rotating the substantially cylindrical substrate and translating the first cutting tool 701 along the proximal shaft portion to form a fifth open surface 129 of the first helical thread 610.

In some embodiments, the manufacturing process may also include rotating the substantially cylindrical substrate and translating the first cutting tool 701 along the distal shaft portion to form a fifth open surface 129 of the second helical thread 620.

In some embodiments, the manufacturing process may also include placing a cutting tool at an intermediate shaft portion of the substantially cylindrical substrate, rotating the substantially cylindrical substrate, and translating the cutting tool along the intermediate shaft portion to form a smooth shaft portion intermediate the first helical thread 610 and the second helical thread 620.

In some embodiments, the first undercut surface 111 and the second undercut surface 112 of the first helical thread 610 may comprise a first concave undercut surface 631 (e.g., see FIG. 6D), the first undercut surface 111 and the second undercut surface 112 of the second helical thread 620 may comprise a second concave undercut surface 632, the third undercut surface 113 and the fourth open surface 114 of the first helical thread 610 may comprise a first convex undercut surface 641, and the third undercut surface 113 and the fourth open surface 114 of the second helical thread 620 may comprise a second convex undercut surface 642.

In some embodiments, the first and second concave undercut surfaces 631, 632 and the first and second convex undercut surfaces 641, 642 may comprise crescent shapes oriented toward one of the proximal end and the distal end of the substantially cylindrical substrate.

In some embodiments, the first and second concave undercut surfaces 631, 632 and the first and second convex undercut surfaces 641, 642 may comprise chevron shapes oriented toward one of the proximal end and the distal end of the substantially cylindrical substrate.

In some embodiments, the first concave undercut surface 631 may comprise a first inflection point 691 at a first inflection point height 695 (e.g., see FIGS. 6D-7D), the first convex undercut surface 641 may comprise a second inflection point 692 at a second inflection point height 696, the second concave undercut surface 632 may comprise a third inflection point 693 at a third inflection point height 697, and the second convex undercut surface 642 may comprise a fourth inflection point 694 at a fourth inflection point height 698.

In some embodiments, the first inflection point height 695 may be equal to the third inflection point height 697, and the second inflection point height 696 may be equal to the fourth inflection point height 698.

In some embodiments, the first pitch 671 of the first helical thread 610 may be less than the second pitch 672 of the second helical thread 620.

In some embodiments, the first pitch 671 of the first helical thread 610 may be greater than the second pitch 672 of the second helical thread 620.

In some embodiments, the first height 681 of the first helical thread 610 may be greater than the second height 682 of the second helical thread 620.

In some embodiments, the first height 681 of the first helical thread 610 may be less than the second height 682 of the second helical thread 620.

In some embodiments, a proximal end 633 of the second helical thread 620 may be timed with a distal end 634 of the first helical thread 620 (e.g., see FIG. 6C, as previously discussed).

In some embodiments, the first pitch 671 of the first helical thread 610 may remain constant irrespective of a selected thickness for the first helical thread 610, as previously discussed.

In some embodiments, the second pitch 672 of the second helical thread 620 may remain constant irrespective of a selected thickness for the second helical thread 620.

In some embodiments, a method for fabricating a compression fastener may generally include forming the first helical thread 610 disposed about a proximal shaft portion of a substantially cylindrical substrate (not shown) and forming the second helical thread 620 disposed about a distal shaft portion of the substantially cylindrical substrate. The first helical thread 610 may include a first inboard portion 811 projecting from the substantially cylindrical substrate at a first height 831, and an outboard portion 812 extending from the first inboard portion 811 at a second height 832 that is greater than the first height 831. The second helical thread 620 may include a second inboard portion 822 that projects from the substantially cylindrical substrate at a third height 833. In some embodiments, the second height 832 of the outboard portion 812 may be greater than the third height 833 of the second inboard portion 822, and the third height 833 of the second inboard portion 822 may be equal to the first height 831 of the first inboard portion 811.

In some embodiments, the first inboard portion 811 of the first helical thread 610 may comprise a first shape and the second inboard portion 822 of the second helical thread 620 may comprise a second shape.

In some embodiments, the first shape and the second shape may be substantially equal to each other.

In some embodiments, the first shape and the second shape may comprise crescent shapes that may be oriented toward one of the proximal end and the distal end of the substantially cylindrical substrate.

In some embodiments, the first shape and the second shape may comprise chevron shapes that may be oriented toward one of the proximal end and the distal end of the substantially cylindrical substrate.

In some embodiments, the first inboard portion 811 may include a first inflection point 691 at a first inflection point height 695, and a second inflection point 692 at a second inflection point height 696.

In some embodiments, the second inboard portion 822 may include a third inflection point 693 at a third inflection point height 697, and a fourth inflection point 694 at a fourth inflection point height 698.

In some embodiments, the first inflection point height 695 may be equal to the third inflection point height 697, and the second inflection point height 696 may be equal to the fourth inflection point height 698.

Any procedures/methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

Any of the implants described or contemplated herein may be configured for removal and replacement during a revision procedure by simply unscrewing and removing the implant from the bone/tissue in which the implant resides. Moreover, the implants described herein may advantageously be removed from bone without removing any appreciable amount of bone during the removal process to preserve the bone. In this manner, implants may be mechanically integrated with the bone, while not being cemented to the bone or integrated via bony ingrowth, in order to provide an instant and removable connection between an implant and a bone. Accordingly, revision procedures utilizing the implants described herein can result in less trauma to the bone and improved patient outcomes. However, it will also be understood that any of the implants described or contemplated herein may also be utilized with cement, as desired.

Reference throughout this specification to "an embodiment" or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, figure, or description thereof for the purpose of streamlining the present disclosure. This method of disclosure, however, is not to be interpreted as reflecting an intention that any embodiment requires more features than those expressly recited in that embodiment. Rather, inventive aspects lie in a combination of fewer than all features of any single foregoing disclosed embodiment.

Recitation of the term "first" with respect to a feature or element does not necessarily imply the existence of a second or additional such feature or element. Elements recited in means-plus-function format are intended to be construed in accordance with 35 U.S.C. § 112(f). It will be apparent to those having skill in the art that changes may be made to the details of the above-described embodiments without departing from the underlying principles set forth herein.

The phrases "connected to," "coupled to" and "in communication with" refer to any form of interaction between two or more entities, including mechanical, electrical, magnetic, electromagnetic, fluid, and thermal interaction. Two components may be functionally coupled to each other even though they are not in direct contact with each other. The term "coupled" can include components that are coupled to each other via integral formation, as well as components that are removably and/or non-removably coupled with each other. The term "abutting" refers to items that may be in direct physical contact with each other, although the items may not necessarily be attached together. The phrase "fluid communication" refers to two or more features that are connected such that a fluid within one feature is able to pass into another feature. Moreover, as defined herein the term "substantially" means within +/−20% of a target value, measurement, or desired characteristic.

While specific embodiments and applications of the present disclosure have been illustrated and described, it is to be understood that the scope of this disclosure is not limited to the precise configuration and components disclosed herein. Various modifications, changes, and variations which will be apparent to those skilled in the art may be made in the arrangement, operation, and details of the devices, systems, and methods disclosed herein.

What is claimed is:

1. A compression fastener comprising:
    a shaft comprising:
        a proximal end;
        a distal end;
        a proximal shaft portion;
        a distal shaft portion; and
        a smooth shaft portion intermediate the proximal shaft portion and the distal shaft portion;
    a helical thread disposed about the shaft, the helical thread comprising:
        at least one concave undercut surface; and
        a plurality of pitches, the plurality of pitches comprising:
            at least one first pitch along the proximal shaft portion; and
            at least one second pitch along the distal shaft portion; and
    a cutting flute formed in the proximal shaft portion and configured to urge bone chips distally toward the smooth shaft portion as the compression fastener is rotated into a bone;
    wherein:
        the at least one concave undercut surface is angled towards one of the proximal end and the distal end of the shaft;
        the at least one first and second pitches are not equal to each other; and
        a first minor diameter of the shaft along the proximal shaft portion is equal to a second minor diameter of the shaft along the distal shaft portion.

2. The compression fastener of claim 1, wherein the plurality of pitches comprises:
    a first discrete pitch along the proximal shaft portion; and
    a second discrete pitch along the distal shaft portion.

3. The compression fastener of claim 2, wherein the first discrete pitch is less than the second discrete pitch.

4. The compression fastener of claim 2, wherein the first discrete pitch is greater than the second discrete pitch.

5. A compression fastener comprising:
    a shaft comprising:
        a proximal end;
        a distal end;
        a proximal shaft portion;
        a distal shaft portion; and
        a smooth shaft portion intermediate the proximal shaft portion and the distal shaft portion;
    a first helical thread disposed about the proximal shaft portion, the first helical thread comprising:
        a first concave undercut surface;
        a first pitch; and
        a first height; and
    a second helical thread disposed about the distal shaft portion, the second helical thread comprising:
        a second concave undercut surface;
        a second pitch; and
        a second height;
    wherein:
        the first concave undercut surface is angled towards one of the proximal end and the distal end of the shaft;
        the second concave undercut surface is angled towards one of the proximal end and the distal end of the shaft;
        the first and second pitches are not equal to each other;
        the first and second heights are not equal to each other;
        the first concave undercut surface comprises a first inflection point at a first inflection point height and a second inflection point at a second inflection point height; and
        the second concave undercut surface comprises a third inflection point at a third inflection point height and a fourth inflection point at a fourth inflection point height,
        wherein the first inflection point height is equal to the third inflection point height, and the second inflection point height is equal to the fourth inflection point height.

6. The compression fastener of claim 5, wherein the first pitch is less than the second pitch.

7. The compression fastener of claim 5, wherein the first pitch is greater than the second pitch.

8. The compression fastener of claim 5, wherein the first height is greater than the second height.

9. The compression fastener of claim 5, wherein a proximal end of the second helical thread is timed with a distal end of the first helical thread.

10. A bone fastener comprising:
    a shaft comprising:
        a proximal end;
        a distal end;
        a proximal shaft portion;
        a distal shaft portion;
    a helical thread disposed about the shaft comprising a concave undercut surface; and
    one or more cutting flutes formed in the bone fastener, wherein:
the concave undercut surface is angled towards one of the proximal end and the distal end of the shaft; and
the one or more cutting flutes are shaped to urge bone chips in at least one direction along the shaft as the bone fastener is rotated into a bone, the one or more cutting flutes comprising:
a first cutting flute formed in the proximal shaft portion; and
a second cutting flute formed in the distal shaft portion,
wherein:
the first cutting flute is configured to urge bone chips in a proximal-to-distal direction along the shaft as the bone fastener is rotated into the bone, and
the second cutting flute is configured to urge bone chips in a distal-to-proximal direction along the shaft as the bone fastener is rotated into the bone.

11. The bone fastener of claim 10, wherein the first cutting flute comprises a plurality of first cutting flutes formed in the proximal shaft portion that are configured to urge bone chips in the proximal-to-distal direction along the shaft as the bone fastener is rotated into the bone.

12. The bone fastener of claim 10, wherein the second cutting flute comprises a plurality of second cutting flutes formed in the distal shaft portion that are configured to urge bone chips in the distal-to-proximal direction along the shaft as the bone fastener is rotated into the bone.

13. The bone fastener of claim 10, wherein the proximal shaft portion comprises one or more proximal reverse cutting flutes.

14. The bone fastener of claim 10, wherein the distal shaft portion comprises one or more distal reverse cutting flutes.

15. The compression fastener of claim 1, wherein a minor diameter of the shaft is constant intermediate the proximal end and the distal end of the shaft.

16. A compression fastener comprising:
a shaft comprising:
a proximal end;
a distal end;
a proximal shaft portion;
a distal shaft portion; and
a smooth shaft portion intermediate the proximal shaft portion and the distal shaft portion;
a first helical thread disposed about the proximal shaft portion, the first helical thread comprising:
a first concave undercut surface positioned on a first side of the first helical thread;
a first convex undercut surface positioned on a second side of the first helical thread;
a first pitch; and
a first height; and
a second helical thread disposed about the distal shaft portion, the second helical thread comprising:
a second concave undercut surface positioned on a first side of the second helical thread;
a second convex undercut surface positioned on a second side of the second helical thread;
a second pitch; and
a second height;
wherein:
a proximal end of the second helical thread is timed with a distal end of the first helical thread;
the first concave undercut surface is angled towards one of the proximal end and the distal end of the shaft;
the second concave undercut surface is angled towards one of the proximal end and the distal end of the shaft;
the first pitch and the second pitch are not equal to each other; and
the first height and the second height are not equal to each other.

17. The compression fastener of claim 16, wherein:
the first pitch comprises a first discrete pitch along the proximal shaft portion; and
the second pitch comprises a second discrete pitch along the distal shaft portion.

18. The compression fastener of claim 17, wherein the first discrete pitch is less than the second discrete pitch.

19. The compression fastener of claim 17, wherein the first discrete pitch is greater than the second discrete pitch.

20. A bone fastener comprising:
a shaft comprising:
a proximal end;
a distal end;
a proximal shaft portion;
a distal shaft portion;
a helical thread disposed about the shaft comprising a concave undercut surface; and
one or more cutting flutes formed in the bone fastener,
wherein:
the concave undercut surface is angled towards one of the proximal end and the distal end of the shaft; and
the one or more cutting flutes are shaped to urge bone chips in at least one direction along the shaft as the bone fastener is rotated into a bone, the one or more cutting flutes comprising:
a first cutting flute formed in the proximal shaft portion; and
a second cutting flute formed in the distal shaft portion,
wherein:
the first cutting flute is configured to urge bone chips in a distal-to-proximal direction along the shaft as the bone fastener is rotated into the bone, and
the second cutting flute is configured to urge bone chips in a proximal-to-distal direction along the shaft as the bone fastener is rotated into the bone.

21. The bone fastener of claim 20, wherein the first cutting flute comprises a plurality of first cutting flutes formed in the proximal shaft portion that are configured to urge bone chips in the distal-to-proximal direction along the shaft as the bone fastener is rotated into the bone.

22. The bone fastener of claim 20, wherein the second cutting flute comprises a plurality of second cutting flutes formed in the distal shaft portion that are configured to urge bone chips in the proximal-to-distal direction along the shaft as the bone fastener is rotated into the bone.

23. The bone fastener of claim 20, wherein the proximal shaft portion comprises one or more proximal reverse cutting flutes.

24. The bone fastener of claim 20, wherein the distal shaft portion comprises one or more distal reverse cutting flutes.

* * * * *